(12) United States Patent
Sharma et al.

(10) Patent No.: US 8,954,165 B2
(45) Date of Patent: Feb. 10, 2015

(54) LEAD ANCHORS AND ASSOCIATED SYSTEMS AND METHODS

(71) Applicant: Nevro Corporation, Menlo Park, CA (US)

(72) Inventors: Vivek Sharma, San Ramon, CA (US); Yougandh Chitre, Santa Clara, CA (US); Andre B. Walker, Monte Sereno, CA (US); Jon Parker, San Jose, CA (US); Ellen Moore, Mountain View, CA (US); Daniel Villamil, Montevideo (UY)

(73) Assignee: Nevro Corporation, Menlo Park, CA (US)

( * ) Notice: Subject to any disclaimer, the term of this patent is extended or adjusted under 35 U.S.C. 154(b) by 0 days.

(21) Appl. No.: 13/750,802

(22) Filed: Jan. 25, 2013

(65) Prior Publication Data

US 2013/0204336 A1 Aug. 8, 2013

Related U.S. Application Data

(60) Provisional application No. 61/590,769, filed on Jan. 25, 2012.

(51) Int. Cl.
*A61N 1/04* (2006.01)
*A61N 1/05* (2006.01)

(52) U.S. Cl.
CPC ....... *A61N 1/0558* (2013.01); *A61N 2001/0582* (2013.01)
USPC ........................................... 607/117; 607/32

(58) Field of Classification Search
CPC ... A61N 1/0558; A61N 1/057; A61N 1/0582; A61N 1/3752; A61B 5/6882; A61B 5/6883; A61B 5/6884

USPC .................... 607/37, 117, 125–127, 130–132
See application file for complete search history.

(56) References Cited

U.S. PATENT DOCUMENTS

| 3,867,950 A | 2/1975 | Fischell |
| 3,982,060 A | 9/1976 | Avery et al. |
| 4,044,774 A | 8/1977 | Corbin et al. |

(Continued)

FOREIGN PATENT DOCUMENTS

| SU | 1648430 A1 | 5/1991 |
| SU | 1690727 A1 | 11/1991 |

(Continued)

OTHER PUBLICATIONS

International Search Report and Written Opinion for International Patent Application No. PCT/US2013/023275, Applicant: Nevro Corporation, mailed May 30, 2013, 6 pages.

(Continued)

*Primary Examiner* — Carl H Layno
*Assistant Examiner* — Eugene Wu
(74) *Attorney, Agent, or Firm* — Perkins Coie LLP

(57) ABSTRACT

The present technology is directed generally to a lead anchor for positioning and securing spinal cord modulation leads and associated systems and methods. In at least some contexts, the lead anchor includes a central lumen surrounded by a restriction feature. The restriction feature can interface with a tightening screw or other actuator and can be configured to provide a radial compressive fit around the lead body. In some embodiments, the clamp can be disengaged upon twisting or other unlocking motion to release the lead.

7 Claims, 16 Drawing Sheets

(56) References Cited

U.S. PATENT DOCUMENTS

| | | | |
|---|---|---|---|
| 4,136,703 | A | 1/1979 | Wittkampf |
| 4,141,365 | A | 2/1979 | Fischell et al. |
| 4,285,347 | A | 8/1981 | Hess |
| 4,328,813 | A | 5/1982 | Ray |
| 4,374,527 | A | 2/1983 | Iversen |
| 4,414,986 | A | 11/1983 | Dickhudt et al. |
| 4,432,377 | A | 2/1984 | Dickhudt |
| 4,462,401 | A | 7/1984 | Burgio |
| 4,462,402 | A | 7/1984 | Burgio et al. |
| 4,465,079 | A | 8/1984 | Dickhudt |
| 4,519,403 | A | 5/1985 | Dickhudt |
| 4,579,120 | A | 4/1986 | MacGregor |
| 4,585,005 | A | 4/1986 | Lue et al. |
| 4,590,942 | A | 5/1986 | Brenman et al. |
| 4,590,949 | A | 5/1986 | Pohndorf |
| 4,633,889 | A | 1/1987 | Talalla et al. |
| 4,658,835 | A | 4/1987 | Pohndorf |
| 4,764,132 | A | 8/1988 | Stutz, Jr. |
| 4,782,837 | A | 11/1988 | Hogan |
| 4,884,579 | A | 12/1989 | Engelson |
| 4,907,602 | A | 3/1990 | Sanders |
| 4,919,653 | A | 4/1990 | Martinez et al. |
| 4,979,511 | A | 12/1990 | Terry, Jr. |
| 4,994,069 | A | 2/1991 | Ritchart et al. |
| 5,000,194 | A | 3/1991 | van den Honert et al. |
| 5,016,647 | A | 5/1991 | Sanders |
| 5,036,862 | A | 8/1991 | Pohndorf |
| 5,167,229 | A | 12/1992 | Peckham et al. |
| 5,179,962 | A | 1/1993 | Dutcher et al. |
| 5,211,165 | A | 5/1993 | Dumoulin et al. |
| 5,215,086 | A | 6/1993 | Terry, Jr. et al. |
| 5,217,484 | A | 6/1993 | Marks |
| 5,231,988 | A | 8/1993 | Wernicke et al. |
| 5,263,480 | A | 11/1993 | Wernicke et al. |
| 5,269,303 | A | 12/1993 | Wernicke et al. |
| 5,273,053 | A | 12/1993 | Pohndorf |
| 5,299,569 | A | 4/1994 | Wernicke et al. |
| 5,312,356 | A | 5/1994 | Engelson et al. |
| 5,325,873 | A | 7/1994 | Hirschi et al. |
| 5,344,438 | A | 9/1994 | Testerman et al. |
| 5,351,687 | A | 10/1994 | Kroll et al. |
| 5,360,441 | A | 11/1994 | Otten |
| 5,417,719 | A | 5/1995 | Hull |
| 5,425,367 | A | 6/1995 | Shapiro et al. |
| 5,464,446 | A | 11/1995 | Dreessen et al. |
| 5,476,494 | A | 12/1995 | Edell et al. |
| 5,480,421 | A | 1/1996 | Otten |
| 5,484,445 | A | 1/1996 | Knuth et al. |
| 5,527,338 | A | 6/1996 | Purdy |
| 5,531,778 | A | 7/1996 | Maschino et al. |
| 5,571,150 | A | 11/1996 | Wernicke et al. |
| 5,669,882 | A | 9/1997 | Pyles |
| 5,693,067 | A | 12/1997 | Purdy |
| 5,728,148 | A | 3/1998 | Bostrom et al. |
| 5,733,322 | A | 3/1998 | Starkebaum |
| 5,746,722 | A * | 5/1998 | Pohndorf et al. ............ 604/175 |
| 5,776,171 | A | 7/1998 | Peckham et al. |
| 5,782,898 | A | 7/1998 | Dahl et al. |
| 5,824,030 | A | 10/1998 | Yang et al. |
| 5,843,146 | A | 12/1998 | Cross, Jr. |
| 5,843,148 | A | 12/1998 | Gijsbers |
| 5,846,226 | A | 12/1998 | Urmey |
| 5,848,126 | A | 12/1998 | Fujita et al. |
| 5,865,843 | A | 2/1999 | Baudino |
| 5,871,487 | A | 2/1999 | Warner et al. |
| 5,871,531 | A | 2/1999 | Struble |
| 5,895,416 | A | 4/1999 | Barreras |
| 5,925,062 | A | 7/1999 | Purdy |
| 5,927,277 | A | 7/1999 | Baudino et al. |
| 5,954,758 | A | 9/1999 | Peckham et al. |
| 5,957,912 | A | 9/1999 | Heitzmann |
| 5,957,965 | A | 9/1999 | Moumane et al. |
| 6,026,328 | A | 2/2000 | Peckham et al. |
| 6,044,304 | A | 3/2000 | Baudino |
| 6,055,456 | A | 4/2000 | Gerber |
| 6,066,165 | A | 5/2000 | Racz |
| 6,104,956 | A | 8/2000 | Naritoku |
| 6,104,960 | A | 8/2000 | Duysens |
| 6,134,477 | A | 10/2000 | Knuteson |
| 6,159,163 | A | 12/2000 | Strauss et al. |
| 6,161,047 | A | 12/2000 | King et al. |
| 6,175,769 | B1 | 1/2001 | Errico et al. |
| 6,192,279 | B1 | 2/2001 | Barreras, Sr. et al. |
| 6,198,963 | B1 | 3/2001 | Haim et al. |
| 6,205,359 | B1 | 3/2001 | Boveja |
| 6,210,417 | B1 | 4/2001 | Baudino et al. |
| 6,233,488 | B1 | 5/2001 | Hess |
| 6,248,080 | B1 | 6/2001 | Miesel et al. |
| 6,248,112 | B1 | 6/2001 | Gambale et al. |
| 6,269,270 | B1 | 7/2001 | Boveja |
| 6,292,695 | B1 | 9/2001 | Webster, Jr. et al. |
| 6,292,702 | B1 | 9/2001 | King et al. |
| 6,304,785 | B1 | 10/2001 | McCreery et al. |
| 6,319,241 | B1 | 11/2001 | King et al. |
| 6,321,104 | B1 | 11/2001 | Gielen et al. |
| 6,325,778 | B1 | 12/2001 | Zadno-Azizi et al. |
| 6,339,725 | B1 | 1/2002 | Naritoku et al. |
| 6,356,788 | B2 | 3/2002 | Boveja |
| 6,360,750 | B1 | 3/2002 | Gerber et al. |
| 6,464,668 | B1 | 10/2002 | Pace |
| 6,473,654 | B1 * | 10/2002 | Chinn ............................ 607/126 |
| 6,549,812 | B1 | 4/2003 | Smits |
| 6,600,956 | B2 | 7/2003 | Maschino et al. |
| 6,601,585 | B1 | 8/2003 | Conrad et al. |
| 6,615,085 | B1 | 9/2003 | Boveja |
| 6,626,181 | B2 | 9/2003 | Knudson et al. |
| 6,634,362 | B2 | 10/2003 | Conrad et al. |
| 6,699,243 | B2 | 3/2004 | West et al. |
| 6,725,096 | B2 | 4/2004 | Chinn et al. |
| 6,733,500 | B2 | 5/2004 | Kelley et al. |
| 6,836,687 | B2 | 12/2004 | Kelley et al. |
| 6,875,571 | B2 | 4/2005 | Crabtree et al. |
| 6,920,359 | B2 | 7/2005 | Meadows et al. |
| 6,934,589 | B2 | 8/2005 | Sundquist et al. |
| 6,937,896 | B1 | 8/2005 | Kroll |
| RE38,972 | E | 2/2006 | Purdy |
| 7,069,083 | B2 | 6/2006 | Finch et al. |
| 7,072,719 | B2 | 7/2006 | Vinup et al. |
| 7,076,305 | B2 | 7/2006 | Imran et al. |
| 7,089,057 | B2 | 8/2006 | Heathershaw et al. |
| 7,090,661 | B2 | 8/2006 | Morris et al. |
| 7,107,097 | B2 | 9/2006 | Stern et al. |
| 7,107,100 | B2 | 9/2006 | Imran et al. |
| 7,107,104 | B2 | 9/2006 | Keravel et al. |
| 7,120,498 | B2 | 10/2006 | Imran et al. |
| 7,146,224 | B2 | 12/2006 | King |
| 7,160,258 | B2 | 1/2007 | Imran et al. |
| 7,164,944 | B1 | 1/2007 | Kroll et al. |
| 7,174,219 | B2 | 2/2007 | Wahlstrand et al. |
| 7,177,702 | B2 | 2/2007 | Wallace et al. |
| 7,177,703 | B2 | 2/2007 | Boveja et al. |
| 7,182,726 | B2 | 2/2007 | Williams et al. |
| 7,184,838 | B2 | 2/2007 | Cross, Jr. |
| 7,184,840 | B2 | 2/2007 | Stolz et al. |
| 7,184,842 | B2 | 2/2007 | Seifert et al. |
| 7,187,982 | B2 | 3/2007 | Seifert et al. |
| 7,191,018 | B2 | 3/2007 | Gielen et al. |
| 7,194,301 | B2 | 3/2007 | Jenkins et al. |
| 7,206,642 | B2 | 4/2007 | Pardo et al. |
| 7,209,787 | B2 | 4/2007 | DiLorenzo |
| 7,212,867 | B2 | 5/2007 | Van Venrooij et al. |
| 7,270,650 | B2 | 9/2007 | Morris et al. |
| 7,277,758 | B2 | 10/2007 | DiLorenzo |
| 7,328,068 | B2 | 2/2008 | Spinelli et al. |
| 7,328,069 | B2 | 2/2008 | Gerber |
| 7,330,762 | B2 | 2/2008 | Boveja et al. |
| 7,337,005 | B2 | 2/2008 | Kim et al. |
| 7,337,006 | B2 | 2/2008 | Kim et al. |
| 7,363,089 | B2 | 4/2008 | Vinup et al. |
| 7,369,894 | B2 | 5/2008 | Gerber |
| 7,379,776 | B1 | 5/2008 | Chitre et al. |
| 7,384,390 | B2 | 6/2008 | Furness et al. |
| 7,386,341 | B2 | 6/2008 | Hafer et al. |
| 7,393,351 | B2 | 7/2008 | Woloszko et al. |

(56) References Cited

U.S. PATENT DOCUMENTS

| | | |
|---|---|---|
| 7,418,292 B2 | 8/2008 | Shafer |
| 7,447,546 B2 | 11/2008 | Kim et al. |
| 7,450,993 B2 | 11/2008 | Kim et al. |
| 7,455,666 B2 | 11/2008 | Purdy |
| 7,460,913 B2 | 12/2008 | Kuzma et al. |
| 7,483,754 B2 | 1/2009 | Imran et al. |
| 7,502,651 B2 | 3/2009 | Kim et al. |
| 7,546,164 B2 | 6/2009 | King |
| 7,547,317 B2 | 6/2009 | Cragg |
| 7,553,307 B2 | 6/2009 | Bleich et al. |
| 7,582,053 B2 | 9/2009 | Gross et al. |
| 7,590,454 B2 | 9/2009 | Garabedian et al. |
| 7,604,644 B2 | 10/2009 | Schulte et al. |
| 7,613,516 B2 | 11/2009 | Cohen et al. |
| 7,684,873 B2 | 3/2010 | Gerber |
| 7,697,972 B2 | 4/2010 | Verard et al. |
| 7,697,995 B2 | 4/2010 | Cross, Jr. et al. |
| 7,702,386 B2 | 4/2010 | Dobak et al. |
| 7,715,924 B2 | 5/2010 | Rezai et al. |
| 7,717,938 B2 | 5/2010 | Kim et al. |
| 7,738,968 B2 | 6/2010 | Bleich |
| 7,742,818 B2 | 6/2010 | Dinsmoor et al. |
| 7,769,442 B2 | 8/2010 | Shafer |
| 7,780,679 B2 | 8/2010 | Bobo, Sr. et al. |
| 7,781,215 B2 | 8/2010 | Ingham et al. |
| 7,797,057 B2 | 9/2010 | Harris |
| 7,810,233 B2 | 10/2010 | Krulevitch et al. |
| 7,810,996 B1 | 10/2010 | Giphart et al. |
| 7,822,482 B2 | 10/2010 | Gerber |
| 7,829,694 B2 | 11/2010 | Kaemmerer |
| 7,854,763 B2 | 12/2010 | Andrieu et al. |
| 7,857,857 B2 | 12/2010 | Kim |
| 7,860,568 B2 * | 12/2010 | Deininger et al. .............. 607/37 |
| 7,904,149 B2 | 3/2011 | Gerber |
| 7,918,849 B2 | 4/2011 | Bleich et al. |
| 7,937,144 B2 | 5/2011 | Dobak |
| 7,967,839 B2 | 6/2011 | Flock et al. |
| 7,987,000 B2 | 7/2011 | Moffitt et al. |
| 7,996,055 B2 | 8/2011 | Hauck et al. |
| 7,998,175 B2 | 8/2011 | Kim |
| 8,000,805 B2 | 8/2011 | Swoyer et al. |
| 8,010,207 B2 | 8/2011 | Smits et al. |
| 8,019,422 B2 | 9/2011 | Imran et al. |
| 8,024,035 B2 | 9/2011 | Dobak, III |
| 8,036,756 B2 | 10/2011 | Swoyer et al. |
| 8,075,595 B2 | 12/2011 | Kim |
| 8,099,172 B2 | 1/2012 | Swanson |
| 8,123,807 B2 | 2/2012 | Kim |
| 8,494,652 B2 | 7/2013 | Cantlon et al. |
| 2001/0014820 A1 | 8/2001 | Gielen et al. |
| 2001/0016765 A1 | 8/2001 | Gielen et al. |
| 2001/0025192 A1 | 9/2001 | Gerber et al. |
| 2001/0027336 A1 | 10/2001 | Gielen et al. |
| 2002/0022872 A1 | 2/2002 | Gielen et al. |
| 2002/0042642 A1 | 4/2002 | Gerber |
| 2002/0087151 A1 | 7/2002 | Mody et al. |
| 2002/0111658 A1 | 8/2002 | Greenberg et al. |
| 2002/0128700 A1 | 9/2002 | Cross |
| 2003/0055476 A1 | 3/2003 | Vinup et al. |
| 2003/0078633 A1 | 4/2003 | Firlik et al. |
| 2003/0097166 A1 | 5/2003 | Krulevitch et al. |
| 2003/0114752 A1 | 6/2003 | Henderson et al. |
| 2003/0114895 A1 | 6/2003 | Gordon et al. |
| 2003/0125786 A1 | 7/2003 | Gliner et al. |
| 2003/0136418 A1 | 7/2003 | Behm |
| 2003/0199949 A1 | 10/2003 | Pardo |
| 2003/0199951 A1 | 10/2003 | Pardo et al. |
| 2003/0199952 A1 | 10/2003 | Stolz et al. |
| 2003/0199953 A1 | 10/2003 | Stolz et al. |
| 2003/0199962 A1 | 10/2003 | Struble et al. |
| 2003/0204228 A1 | 10/2003 | Cross et al. |
| 2003/0208247 A1 | 11/2003 | Spinelli et al. |
| 2003/0220677 A1 | 11/2003 | Doan et al. |
| 2004/0024440 A1 | 2/2004 | Cole |
| 2004/0049240 A1 | 3/2004 | Gerber et al. |
| 2004/0088033 A1 | 5/2004 | Smits et al. |
| 2004/0088034 A1 | 5/2004 | Smits et al. |
| 2004/0093051 A1 | 5/2004 | Chinn et al. |
| 2004/0093053 A1 | 5/2004 | Gerber et al. |
| 2004/0097803 A1 | 5/2004 | Panescu |
| 2004/0147976 A1 | 7/2004 | Gordon et al. |
| 2004/0162601 A1 | 8/2004 | Smits |
| 2004/0186543 A1 | 9/2004 | King et al. |
| 2004/0186544 A1 | 9/2004 | King |
| 2004/0193228 A1 | 9/2004 | Gerber |
| 2004/0215301 A1 | 10/2004 | Lokhoff et al. |
| 2004/0215307 A1 | 10/2004 | Michels et al. |
| 2004/0236387 A1 | 11/2004 | Fang et al. |
| 2004/0243101 A1 | 12/2004 | Gillis |
| 2004/0243206 A1 | 12/2004 | Tadlock |
| 2005/0004417 A1 | 1/2005 | Nelson et al. |
| 2005/0004638 A1 | 1/2005 | Cross |
| 2005/0010260 A1 | 1/2005 | Gerber |
| 2005/0015128 A1 | 1/2005 | Rezai et al. |
| 2005/0020970 A1 | 1/2005 | Gerber |
| 2005/0027338 A1 | 2/2005 | Hill |
| 2005/0033372 A1 | 2/2005 | Gerber |
| 2005/0033373 A1 | 2/2005 | Gerber |
| 2005/0033374 A1 | 2/2005 | Gerber |
| 2005/0049648 A1 | 3/2005 | Cohen et al. |
| 2005/0055064 A1 | 3/2005 | Meadows et al. |
| 2005/0065588 A1 | 3/2005 | Zhao et al. |
| 2005/0070969 A1 | 3/2005 | Gerber |
| 2005/0070974 A1 | 3/2005 | Knudson et al. |
| 2005/0075684 A1 | 4/2005 | Phillips et al. |
| 2005/0075702 A1 | 4/2005 | Shafer |
| 2005/0075707 A1 | 4/2005 | Meadows et al. |
| 2005/0090885 A1 | 4/2005 | Harris et al. |
| 2005/0096750 A1 | 5/2005 | Kagan et al. |
| 2005/0101977 A1 | 5/2005 | Gannoe et al. |
| 2005/0113878 A1 | 5/2005 | Gerber |
| 2005/0131506 A1 | 6/2005 | Rezai et al. |
| 2005/0137644 A1 | 6/2005 | Boveja et al. |
| 2005/0148951 A1 | 7/2005 | Gonon |
| 2005/0149157 A1 | 7/2005 | Hunter et al. |
| 2005/0165465 A1 | 7/2005 | Pianca et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182424 A1 | 8/2005 | Schulte et al. |
| 2005/0182425 A1 | 8/2005 | Schulte et al. |
| 2005/0182455 A1 | 8/2005 | Thrope et al. |
| 2005/0182463 A1 | 8/2005 | Hunter et al. |
| 2005/0182467 A1 | 8/2005 | Hunter et al. |
| 2005/0182468 A1 | 8/2005 | Hunter et al. |
| 2005/0182469 A1 | 8/2005 | Hunter et al. |
| 2005/0183731 A1 | 8/2005 | Hunter et al. |
| 2005/0187600 A1 | 8/2005 | Hunter et al. |
| 2005/0192647 A1 | 9/2005 | Hunter et al. |
| 2005/0196421 A1 | 9/2005 | Hunter et al. |
| 2005/0203599 A1 | 9/2005 | Garabedian et al. |
| 2005/0203600 A1 | 9/2005 | Wallace et al. |
| 2005/0209665 A1 | 9/2005 | Hunter et al. |
| 2005/0209667 A1 | 9/2005 | Erickson et al. |
| 2005/0215942 A1 | 9/2005 | Abrahamson et al. |
| 2005/0222642 A1 | 10/2005 | Przybyszewski et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0228221 A1 | 10/2005 | Hirakawa |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0251237 A1 | 11/2005 | Kuzma et al. |
| 2005/0283053 A1 | 12/2005 | deCharms |
| 2006/0004429 A1 | 1/2006 | Mrva et al. |
| 2006/0041277 A1 | 2/2006 | Deem et al. |
| 2006/0041295 A1 | 2/2006 | Osypka |
| 2006/0052765 A1 | 3/2006 | Pyles et al. |
| 2006/0052836 A1 | 3/2006 | Kim et al. |

(56) References Cited

U.S. PATENT DOCUMENTS

| | | |
|---|---|---|
| 2006/0084982 A1 | 4/2006 | Kim |
| 2006/0084983 A1 | 4/2006 | Kim |
| 2006/0085069 A1 | 4/2006 | Kim |
| 2006/0085070 A1 | 4/2006 | Kim |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0095134 A1 | 5/2006 | Trieu et al. |
| 2006/0122620 A1 | 6/2006 | Kim |
| 2006/0122678 A1 | 6/2006 | Olsen et al. |
| 2006/0161235 A1 | 7/2006 | King |
| 2006/0161236 A1 | 7/2006 | King |
| 2006/0167525 A1 | 7/2006 | King |
| 2006/0168805 A1 | 8/2006 | Hegland et al. |
| 2006/0173262 A1 | 8/2006 | Hegland et al. |
| 2006/0206118 A1 | 9/2006 | Kim et al. |
| 2006/0224102 A1 | 10/2006 | Glenn |
| 2006/0247747 A1 | 11/2006 | Olsen et al. |
| 2006/0247748 A1 | 11/2006 | Wahlstrand et al. |
| 2006/0247776 A1 | 11/2006 | Kim |
| 2006/0253182 A1 | 11/2006 | King |
| 2006/0259110 A1 | 11/2006 | Wallace et al. |
| 2006/0265039 A1 | 11/2006 | Bartic et al. |
| 2007/0005140 A1 | 1/2007 | Kim et al. |
| 2007/0021786 A1 | 1/2007 | Parnis et al. |
| 2007/0027486 A1 | 2/2007 | Armstrong |
| 2007/0027514 A1 | 2/2007 | Gerber |
| 2007/0027515 A1 | 2/2007 | Gerber |
| 2007/0032836 A1 | 2/2007 | Thrope et al. |
| 2007/0050004 A1 | 3/2007 | Swoyer et al. |
| 2007/0050005 A1 | 3/2007 | Lauro |
| 2007/0055332 A1 | 3/2007 | Swoyer |
| 2007/0060973 A1 | 3/2007 | Ludvig et al. |
| 2007/0073355 A1 | 3/2007 | DiLorenzo |
| 2007/0088414 A1 | 4/2007 | Campbell et al. |
| 2007/0100408 A1 | 5/2007 | Gerber |
| 2007/0106289 A1 | 5/2007 | O'Sullivan |
| 2007/0112404 A1 | 5/2007 | Mann et al. |
| 2007/0123888 A1 | 5/2007 | Bleich et al. |
| 2007/0135881 A1 | 6/2007 | Vilims |
| 2007/0150036 A1 | 6/2007 | Anderson |
| 2007/0161919 A1 | 7/2007 | DiLorenzo |
| 2007/0162085 A1 | 7/2007 | DiLorenzo |
| 2007/0168008 A1 | 7/2007 | Olsen |
| 2007/0179580 A1 | 8/2007 | Colborn |
| 2007/0191904 A1 | 8/2007 | Libbus et al. |
| 2007/0198063 A1 | 8/2007 | Hunter et al. |
| 2007/0203540 A1 | 8/2007 | Goetz et al. |
| 2007/0213795 A1 | 9/2007 | Bradley et al. |
| 2007/0244520 A1 | 10/2007 | Ferren et al. |
| 2007/0255340 A1 | 11/2007 | Giftakis et al. |
| 2007/0255341 A1 | 11/2007 | Giftakis et al. |
| 2007/0255364 A1 | 11/2007 | Gerber et al. |
| 2007/0255365 A1 | 11/2007 | Gerber et al. |
| 2007/0255366 A1 | 11/2007 | Gerber et al. |
| 2007/0255367 A1 | 11/2007 | Gerber et al. |
| 2007/0255368 A1 | 11/2007 | Bonde et al. |
| 2007/0255369 A1 | 11/2007 | Bonde et al. |
| 2007/0255383 A1 | 11/2007 | Gerber et al. |
| 2007/0261115 A1 | 11/2007 | Gerber et al. |
| 2007/0276450 A1 | 11/2007 | Meadows et al. |
| 2008/0027505 A1 | 1/2008 | Levin et al. |
| 2008/0046036 A1 | 2/2008 | King et al. |
| 2008/0103569 A1 | 5/2008 | Gerber |
| 2008/0103570 A1 | 5/2008 | Gerber |
| 2008/0103572 A1 | 5/2008 | Gerber |
| 2008/0103576 A1 | 5/2008 | Gerber |
| 2008/0103578 A1 | 5/2008 | Gerber |
| 2008/0103579 A1 | 5/2008 | Gerber |
| 2008/0103580 A1 | 5/2008 | Gerber |
| 2008/0140087 A1 | 6/2008 | Barbagli |
| 2008/0140152 A1 | 6/2008 | Imran et al. |
| 2008/0140169 A1 | 6/2008 | Imran |
| 2008/0147156 A1 | 6/2008 | Imran |
| 2008/0177339 A1 | 7/2008 | Bolea et al. |
| 2008/0177364 A1 | 7/2008 | Bolea et al. |
| 2008/0183221 A1 | 7/2008 | Burdulis |
| 2008/0183224 A1 | 7/2008 | Barolat |
| 2008/0183257 A1 | 7/2008 | Imran et al. |
| 2008/0216846 A1 | 9/2008 | Levin |
| 2008/0243218 A1 | 10/2008 | Bottomley et al. |
| 2008/0275467 A1 | 11/2008 | Liao et al. |
| 2008/0319311 A1 | 12/2008 | Hamadeh |
| 2009/0018630 A1 | 1/2009 | Osypka et al. |
| 2009/0024075 A1 | 1/2009 | Schroeppel et al. |
| 2009/0099439 A1 | 4/2009 | Barolat |
| 2009/0112272 A1 | 4/2009 | Schleicher et al. |
| 2009/0112301 A1 | 4/2009 | Kowalczyk |
| 2009/0204119 A1 | 8/2009 | Bleich et al. |
| 2009/0216306 A1 | 8/2009 | Barker |
| 2009/0270940 A1* | 10/2009 | Deininger et al. ............ 607/37 |
| 2010/0004654 A1 | 1/2010 | Schmitz et al. |
| 2010/0036454 A1 | 2/2010 | Bennett et al. |
| 2010/0057162 A1 | 3/2010 | Moffitt et al. |
| 2010/0057163 A1 | 3/2010 | Moffitt et al. |
| 2010/0057164 A1 | 3/2010 | Moffitt et al. |
| 2010/0057165 A1 | 3/2010 | Moffitt et al. |
| 2010/0057177 A1 | 3/2010 | Moffitt et al. |
| 2010/0070010 A1 | 3/2010 | Simpson |
| 2010/0094231 A1 | 4/2010 | Bleich et al. |
| 2010/0100158 A1 | 4/2010 | Thrope et al. |
| 2010/0137943 A1 | 6/2010 | Zhu |
| 2010/0137944 A1 | 6/2010 | Zhu |
| 2010/0145221 A1 | 6/2010 | Brunnett et al. |
| 2010/0145427 A1 | 6/2010 | Gliner et al. |
| 2010/0152538 A1 | 6/2010 | Gleason et al. |
| 2010/0179562 A1 | 7/2010 | Linker et al. |
| 2010/0256720 A1 | 10/2010 | Overstreet et al. |
| 2010/0274314 A1 | 10/2010 | Alataris et al. |
| 2010/0274315 A1 | 10/2010 | Alataris et al. |
| 2010/0274326 A1 | 10/2010 | Chitre et al. |
| 2010/0274336 A1 | 10/2010 | Nguyen-Stella et al. |
| 2010/0292769 A1 | 11/2010 | Brounstein et al. |
| 2010/0298905 A1 | 11/2010 | Simon |
| 2010/0312319 A1 | 12/2010 | Barker |
| 2010/0318165 A1 | 12/2010 | Harris |
| 2011/0022114 A1 | 1/2011 | Navarro |
| 2011/0022141 A1 | 1/2011 | Chen et al. |
| 2011/0022142 A1 | 1/2011 | Barker et al. |
| 2011/0022143 A1 | 1/2011 | North |
| 2011/0031961 A1 | 2/2011 | Durand et al. |
| 2011/0046617 A1 | 2/2011 | Thompson et al. |
| 2011/0071540 A1 | 3/2011 | Kast et al. |
| 2011/0071593 A1 | 3/2011 | Parker et al. |
| 2011/0071604 A1 | 3/2011 | Wahlstrand et al. |
| 2011/0106052 A1 | 5/2011 | Chiang et al. |
| 2011/0112609 A1 | 5/2011 | Peterson |
| 2011/0144468 A1 | 6/2011 | Boggs et al. |
| 2011/0224710 A1 | 9/2011 | Bleich |
| 2011/0230943 A1 | 9/2011 | Johnson et al. |
| 2012/0083709 A1 | 4/2012 | Parker et al. |

FOREIGN PATENT DOCUMENTS

| | | |
|---|---|---|
| WO | WO-9003824 A1 | 4/1990 |
| WO | WO-2008094952 A2 | 8/2008 |

OTHER PUBLICATIONS

"Clik Anchor SC-4316," Boston Scientific Corporation, 2011, 1 page.

Medtronic, "Physician and Hospital Staff Manual," InterStrim System, Neurological Division. 93 pages, undated.

Intrel® Model 7490 / 7491 Extensions for Spinal Cord Stimulation (SCS), Medtronic Neuro, Minneapolis, MN 1984, 9 pages.

Kumar et al., "Spinal Cord Stimulation in Treatment of Chronic Benign Pain: Challenges in Treatment ; Planning and Present Status, a 22-Year Experience," Neurosurgery, vol. 58, No. 3, Mar. 2006, ; 16 pages.

* cited by examiner

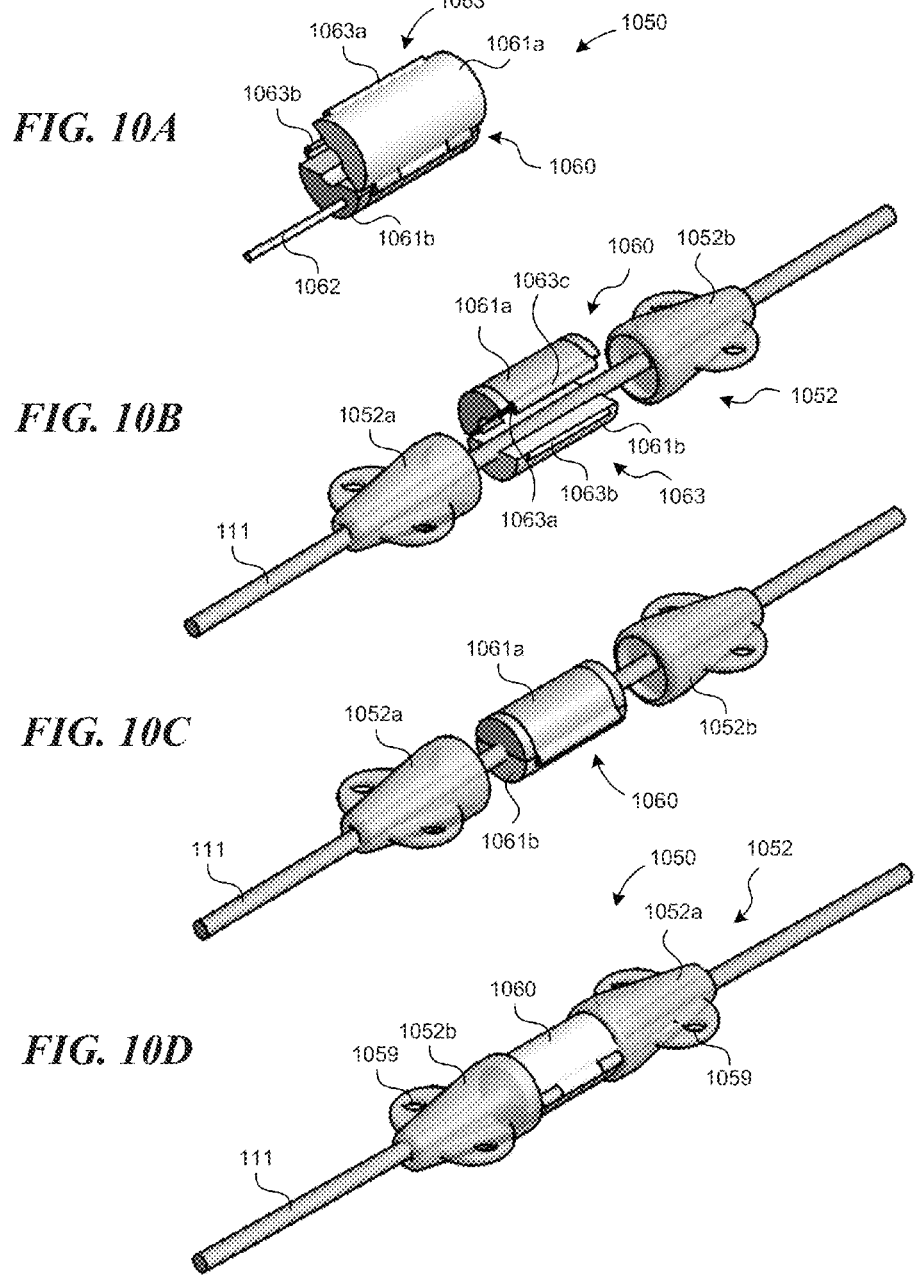

LEAD ANCHORS AND ASSOCIATED SYSTEMS AND METHODS

CROSS-REFERENCE TO RELATED APPLICATION

The present application claims priority to U.S. Provisional Application 61/590,769, filed on Jan. 25, 2012 and incorporated herein by reference.

TECHNICAL FIELD

The present technology is directed generally to lead anchors for positioning and securing spinal cord modulation leads or other signal delivery elements as well as associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes or contacts and the SCS leads are typically implanted either surgically or percutaneously through a large needle inserted into the epidural space, often with the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. During pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations.

In any of the foregoing systems, it is important for the practitioner to accurately position and anchor the leads in order to provide effective therapy. Existing lead anchors can negatively impact lead performance and/or reliability when they allow the lead body to slide or otherwise change position. The movement of the lead body relative to the lead anchor can reduce the accuracy with which the stimulation is provided, thus limiting the effectiveness of the therapy. In some cases, the leads must be securely fixed but still repositionable if the practitioner determines that a different position would provide more effective therapy. Reliable retention of the leads or other signal delivery elements in the pulse generator, lead extension components, as well as components that may releasably couple a lead or other signal delivery element to an external stimulator (such as those disclosed in co-pending U.S. Patent Application Publication No. 2011/0071593 to Parker et al., which is hereby incorporated by reference in its entirety) is also important in such systems. As a result, there exists a need for a lead retention mechanism, such as a lead anchor, etc, that mitigates lead movement while providing the ability to subsequently reposition the lead.

BRIEF DESCRIPTION OF THE DRAWINGS

FIGS. 10A-10D are partially schematic, isometric illustrations of a lead securement device having a clamshell configuration in accordance with an embodiment of the present technology.

DETAILED DESCRIPTION

The present technology is directed generally to lead anchors for positioning and securing spinal cord modulation leads or other signal delivery elements as well as associated systems and methods. In at least some contexts, the lead anchor includes a central lumen surrounded or partially surrounded by a restriction feature. The restriction feature can interface with a tightening screw and can be configured to provide a compressive fit on or around the lead body. In some embodiments, the restriction feature can be disengaged by twisting or otherwise imparting an unlocking motion to release the lead. Other embodiments may eliminate particular components or procedures described herein. A person of ordinary skill in the relevant art, therefore, will understand that the present technology may include other embodiments with additional elements, and/or may include other embodiments without several of the features shown and described below with reference to FIGS. 1A-11E. Several aspects of overall systems in accordance with the disclosed technology are described with reference to FIGS. 1A and 1B, and features specific to representative lead anchors are then discussed with reference to FIGS. 2A-11E.

Figure 1A:
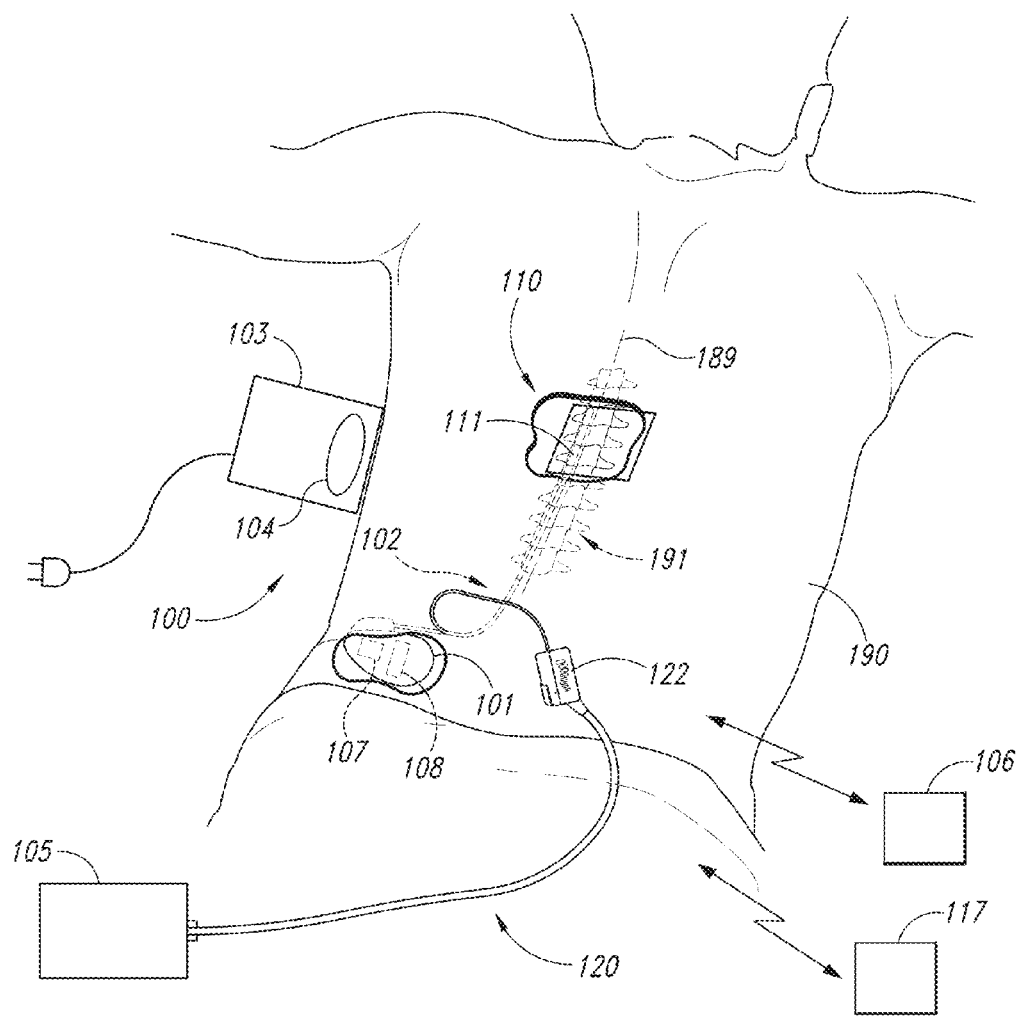
FIG. 1A is a partially schematic illustration of an implantable spinal cord modulation system positioned at a patient's spine to deliver therapeutic signals in accordance with several embodiments of the present technology.

FIG. 1A schematically illustrates a representative patient system 100 for providing relief from chronic pain and/or other conditions, arranged relative to the general anatomy of a patient's spinal cord 191. The overall patient system 100 can include a signal delivery device 110, which may be implanted within a patient 190, typically at or near the patient's midline 189, and which is coupled to a pulse generator 101. The signal delivery device 110 carries features for delivering therapy to the patient 190 after implantation. The pulse generator 101 can be connected directly to the signal delivery device 110, or it can be coupled to the signal delivery device 110 via a signal link 102 (e.g., an extension). In a further representative embodiment, the signal delivery device 110 can include an elongated lead or lead body 111. As used herein, the terms "lead" and "lead body" include any of a number of suitable substrates and/or support members that carry devices for providing therapy signals to the patient 190. For example, the lead 111 can include one or more electrodes or electrical contacts at a distal end that direct electrical signals into the patient's tissue, such as to provide for patient relief. As will be described in further detail below with reference to FIGS. 2A-11E, a portion of the lead 111 can be anchored to the patient.

The pulse generator 101 can transmit signals (e.g., electrical signals) to the signal delivery device 110 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing modulation signals, providing guidance information for locating the signal delivery device 110, and/or executing other associated functions can be performed by computer-executable instructions contained by computer-readable media located at the pulse generator 101 and/or other system components. The pulse generator 101 can include multiple portions, elements, and/or subsystems (e.g., for directing signals in accordance with multiple signal delivery parameters), carried in a single housing, as shown in FIG. 1A, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

During at least some procedures, an external programmer 105 (e.g., a trial modulator) can be coupled to the signal delivery device 110 during an initial procedure, prior to implanting the pulse generator 101. For example, a practitioner (e.g., a physician and/or a company representative) can use the external programmer 105 to vary the modulation parameters provided to the signal delivery device 110 in real time, and select optimal or particularly efficacious parameters. These parameters can include the location from which the electrical signals are emitted, as well as the characteristics of the electrical signals provided to the signal delivery device 110. In a typical process, the practitioner uses a cable assembly 120 to temporarily connect the external programmer 105 to the signal delivery device 110. The practitioner can test the efficacy of the signal delivery device 110 in an initial position. The practitioner can then disconnect the cable assembly 120 (e.g., at a connector 122), reposition the signal delivery device 110, and reapply the electrical modulation. This process can be performed iteratively until the practitioner obtains the desired position for the signal delivery device 110. Optionally, the practitioner may move the partially implanted signal delivery element 110 without disconnecting the cable assembly 120.

After a trial period with the external programmer 105, the practitioner can implant the implantable pulse generator 101 within the patient 190 for longer term treatment. The signal delivery parameters provided by the pulse generator 101 can still be updated after the pulse generator 101 is implanted, via a wireless physician's programmer 117 (e.g., a physician's remote) and/or a wireless patient programmer 106 (e.g., a patient remote). Generally, the patient 190 has control over fewer parameters than does the practitioner. In other embodiments, the iterative trial process described above can be eliminated, e.g., when an initial implant provides a suitable therapeutic effect without the need for a trial process.

Figure 1B:
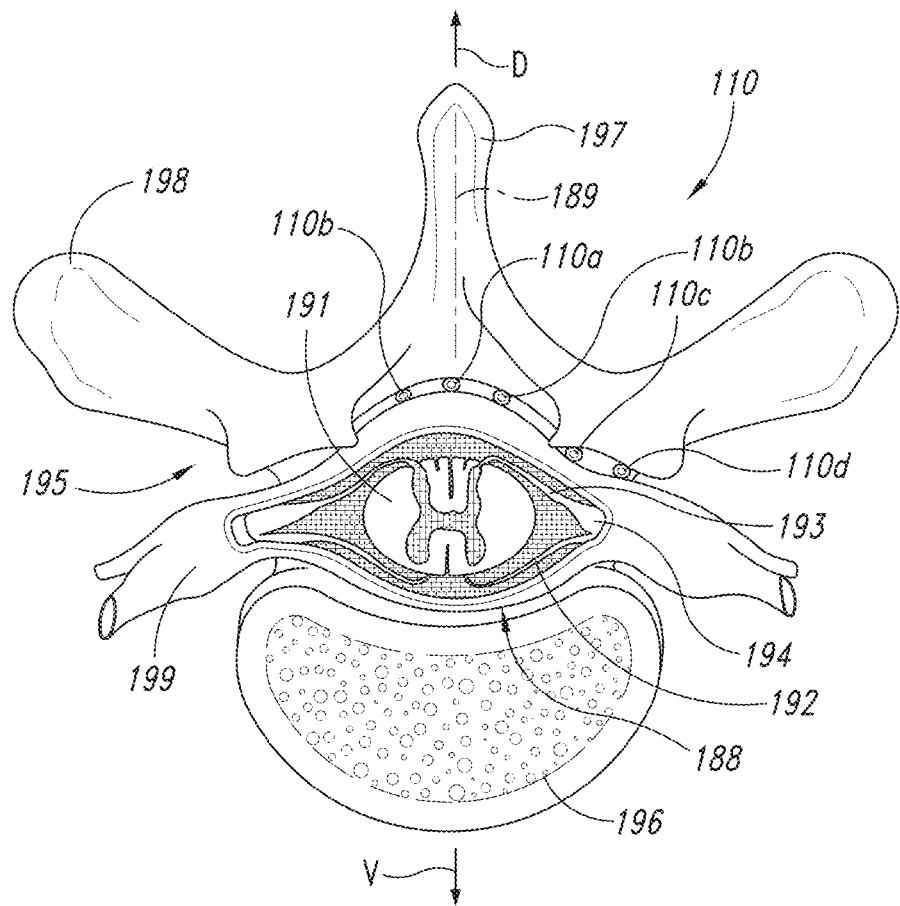
FIG. 1B is a partially schematic, cross-sectional illustration of a patient's spine, illustrating representative locations for an implanted lead in accordance with embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 110 (shown as signal delivery devices 110a-d) implanted at representative locations. For purposes of illustration, multiple signal delivery devices 110 are shown in FIG. 1B implanted in a single patient. In actual use, any given patient will likely receive fewer than all the signal delivery devices 110 shown in FIG. 1B.

The spinal cord 191 is situated within a vertebral foramen 188, between a ventrally-located ventral body 196 and a dorsally-located transverse process 198 and spinous process

197. Arrows V and D identify the ventral and dorsal directions, respectively. The spinal cord 191 is located within the dura mater 199, which also surrounds portions of the nerves exiting the spinal cord 191, including the ventral roots 192, dorsal roots 193 and dorsal root ganglia 194. In one embodiment, a single first signal delivery device 110*a* is positioned within the vertebral foramen 188, at or approximately at the spinal cord midline 189. In another embodiment, two second signal delivery devices 110*b* are positioned just off the spinal cord midline 189 (e.g., about 1 mm. offset) in opposing lateral directions so that the two signal delivery devices 110*b* are spaced apart from each other by about 2 mm. In still further embodiments, a single signal delivery device or pairs of signal delivery devices can be positioned at other locations, e.g., at the dorsal root entry zone as shown by a third signal delivery device 110*c*, or at the dorsal root ganglia 194, as shown by a fourth signal delivery device 110*d*.

In any of the foregoing embodiments, it is important that the signal delivery device 110 and, in particular, the electrical contacts of the device, be placed at a target location that is expected (e.g., by a practitioner) to produce efficacious results in the patient when the device 110 is activated. The following disclosure describes techniques and systems for securing signal delivery devices 110 at target modulation sites, and/or otherwise securing connections between elements of the systems, and/or between system elements and the patient's body. Particular embodiments are described below in the context of securing a lead relative to the patient's tissue. In other embodiments, similar or identical arrangements are used to secure a lead or lead extension to an implanted pulse generator or external modulation device, to secure a lead to a lead extension, to secure a lead or lead extension to an operating room cable (e.g., at the connector 122 described above), and/or to perform other securement functions, e.g., in the context of neural modulation.

Figure 2A:
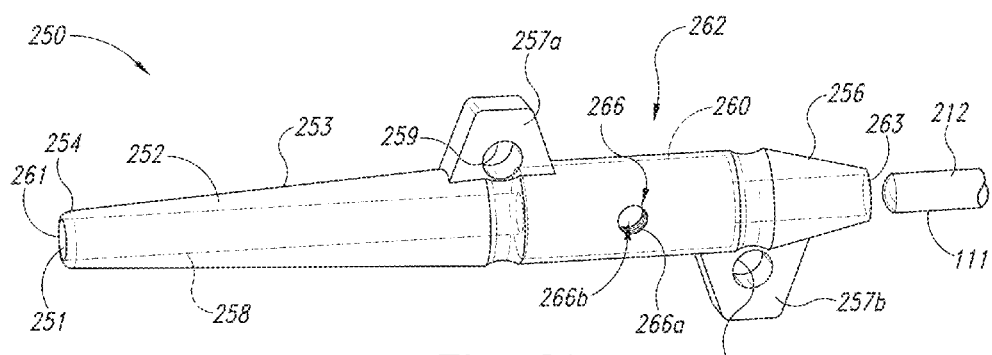
FIG. 2A is an isometric illustration of a lead anchor configured in accordance with embodiments of the present technology.

FIG. 2A is an isometric illustration of a lead anchor 250 having features in accordance with embodiments of the disclosure. The lead anchor 250 can releasably attach a lead (e.g., the lead 111 illustrated in FIG. 1A) or other signal delivery element to tissue adjacent to or in the epidural space around the spinal cord. The anchor 250 includes an anchor sleeve 252 having a distal end 254, a proximal end 256, an exterior surface 253, and a longitudinally-extending lumen 258. The lumen 258 has an interior surface 251 extending from a distal end opening 261 at the distal end 254 to a proximal end opening 263 at the proximal end 256. The lead 111 can be inserted into the lumen 258 so as to extend through the anchor sleeve 252 from the proximal end opening 263 to the distal end opening 261. As will be described in further detail below with reference to FIG. 2B, the anchor 250 further includes a lead securement region 262 at which a lead securement device 260 is located. The lead securement device 260 can engage and secure the lead 111 when the lead 111 is positioned in the lumen 258.

The lead anchor 250 can include an aperture 266 extending inwardly from the exterior surface 253. The aperture 266 can include a first portion 266*a* that extends to the interior surface 251 of the anchor sleeve 252, e.g., transverse to the major axis of the lumen 258. The aperture 266 can also include a second portion 266*b*, aligned with the first portion 266*a* and extending into the lead securement device 260. Accordingly, and as will be discussed in further detail below with reference to FIG. 2B, the aperture 266 can provide a practitioner with access to the lead securement device 260. In certain embodiments, such as those described below with reference to FIGS. 3 and 4, the lead anchor 250 can include more than one aperture 266 extending through the anchor sleeve 252. In some embodiments, the anchor sleeve 252 is made of plastic, metal, silicone, another biocompatible material, and/or a combination of materials. In certain embodiments, the anchor sleeve 252 can include a radiopaque marker (e.g., an embedded platinum or metallic component) to aid the practitioner in positioning the anchor sleeve 252. In the illustrated embodiment, the anchor sleeve 252 is generally tapered toward both the distal and proximal ends 254, 256. In further embodiments, the anchor sleeve 252 is not tapered, or only one of the distal or proximal ends 254, 256 is tapered, or the anchor sleeve 252 can widen toward the distal and/or proximal ends 254, 256.

One or more tissue-securing features 257 (identified individually as first and second tissue-securing features 257*a*, 257*b*) can secure the anchor 250 to the patient. In the illustrated embodiment, the tissue-securing features 257*a*, 257*b* extend laterally from the anchor sleeve 252 and include eyelets 259 through which the practitioner can loop a suturing thread (not shown) to affix the anchor 250 to a patient's tissue. In various embodiments, the anchor 250 can have more or fewer eyelets 259 or other fastening features, and/or the tissue-securing features 257*a*, 257*b* can be located at additional or other positions on the anchor sleeve 252.

In certain embodiments, at least a portion of an external surface 212 of the lead 111, or the interior surface 251 of the anchor sleeve 252 can have features (e.g., roughness features), coatings, and/or other elements to increase a coefficient of friction between the lead 111 and the interior surface 251 of the anchor sleeve 252. In some embodiments, for example, the lead 111 and/or the interior surface 251 of the anchor sleeve 252 can include bulges or other friction features, and/or can comprise a high-friction material (e.g., rubber), and/or can be laser or chemically etched to increase friction. Furthermore, in certain embodiments, the lead 111 can include barbs, extensions, protrusions and/or other features that can engage the interior surface 251 of the anchor sleeve 252, e.g., to releaseably affix the lead within the anchor sleeve 252.

Figure 2B:
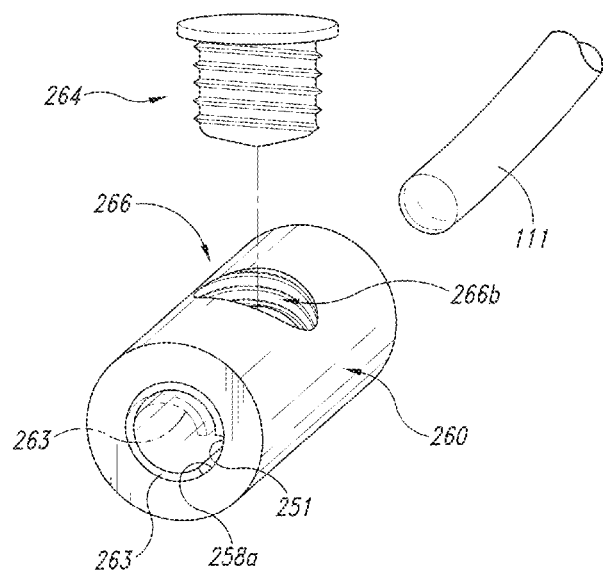
FIG. 2B is an isometric illustration of a locking mechanism for securing a lead anchor in accordance with embodiments of the present technology.

FIG. 2B illustrates a representative lead securement device 260 that can be housed in the sleeve 252 described above. Depending upon the particular embodiments, the securement device 260 may be used to secure a lead or other signal delivery element in a pulse generator, a lead extension component, or a component that may releasably couple a lead or other signal delivery element to an external stimulator. In this embodiment, the lead securement device 260 is configured to clamp or otherwise secure the lead 111 in position. The securement device 260 can accordingly include a restriction member 263 and an actuator, e.g., a set screw 264, configured to actuate the restriction member 263. For purposes of illustration, the actuator is shown as a set screw in many of the Figures. In other embodiments, the actuator can have other suitable threaded or unthreaded configurations. The securement device 260 includes a device lumen 258*a* that receives the restriction member 263 and is aligned to be co-axial with the lumen 258 in the anchor sleeve 252 (FIG. 2A). The restriction member 263 can be accessible via the second portion 266*b* of the aperture 266. The restriction member 263 can comprise a medical grade metal or alloy thereof (e.g., stainless steel, nickel titanium, or nickel-cobalt-molybdenum alloys such as MP35N, etc.), and/or another biocompatible material. In the illustrated embodiment, the restriction member 263 takes the form of a sheet and has a C-shape in cross-section when deployed to extend around only a portion of the circumference of the interior surface 251 of the device lumen 258*a* as shown in FIG. 2B. The restriction member 263 can accordingly form a radially compressible collet within the device lumen 258a and around the lead 111. The set screw 264 can be sized to threadably engage with threads in the second portion 266b of the aperture 266 to engage the restriction member 263. Accordingly, the practitioner can tighten the set screw 264 against the restriction member 262, which in turn clamps against the lead 111.

Referring to FIGS. 2A and 2B together, the practitioner in use can introduce the lead 111 into the patient's body with a stylet, introducer, or other suitable device. The practitioner then threads the lead anchor 250 along the lead 111, and secures the anchor 250 to the lead 111 by advancing the set screw 264 (located in the aperture 266) radially inward. As the set screw 264 advances and engages with the restriction member 263, the restriction member 263 exerts a radial clamping force on the lead 111. The practitioner can vary the degree to which the restriction member 263 compresses the lead 111. In some embodiments, the set screw 264 can be advanced into the aperture 266 by a torque wrench that clicks upon applying a preset level of torque. The practitioner can then secure the anchor 250 in place by suturing the anchor 250 to the tissue, using the eyelets 259 in the tissue-securing features 257a, 257b.

If the practitioner wishes to reposition the lead 111 (e.g., to adjust the positions of the modulation contacts for improved treatment), the practitioner can release the connection between the anchor 250 and the lead 111 without having to detach the anchor 250 from the patient. For example, the practitioner can turn the set screw 264 in the reverse direction to provide less compressive force on the restriction member 263. In other embodiments, a twisting or unlocking motion can disengage the restriction member 263 and release the compressive force on the lead 111. The restriction member 263 can be at least partially restored to its original cross-sectional shape after the set screw 264 is removed or loosened. Once the restriction member 263 has been loosened, the practitioner can reposition the lead 111 relative to the anchor 250. Once the lead 111 has been repositioned, the practitioner can tighten the set screw 264 in the manner described above, and can then apply an electrical modulation therapy to the patient.

Figure 2C:
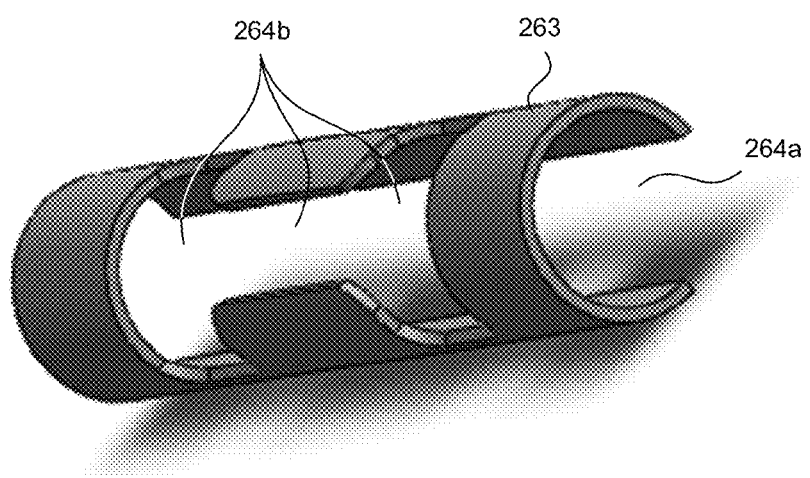
FIG. 2C is an isometric illustration of a restriction member configured in accordance with an embodiment of the presently disclosed technology.

FIG. 2C is a partially schematic, isometric view of a restriction member 263 configured in accordance with a representative embodiment. The restriction member 263 can include an axially-extending gap 264a that allows the restriction member 263 to tighten around the lead, as discussed above. The restriction member 263 can also include one or more slots or cut-outs 264b that can be formed to reduce the volume/weight of the restriction member 263 and/or control the flexibility of the restriction member 263.

Figure 3:
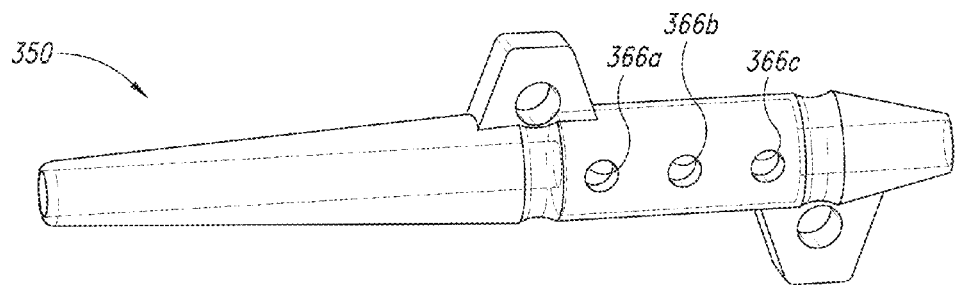
FIGS. 3 and 4 illustrate embodiments of lead anchors having multiple apertures in accordance with further embodiments of the technology.
Figure 4:
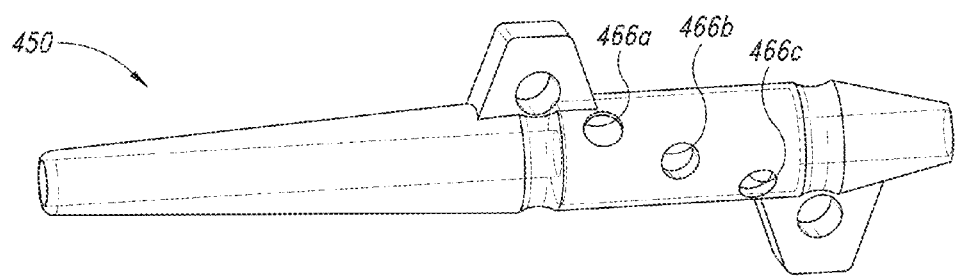

FIGS. 3 and 4 are isometric illustrations of lead anchors configured in accordance with further embodiments of the present technology. Referring first to FIG. 3, a representative lead anchor 350 has several features generally similar to those described above with reference to FIGS. 2A and 2B. The lead anchor 350 further includes a plurality of apertures, identified individually as apertures 366a-366c. In the illustrated embodiment, the apertures 366a-366c are longitudinally aligned. The multiple apertures 366a-366c allow a practitioner to clamp a lead at one or more of several locations by applying a compressive force via one or more of a plurality of actuators (e.g., multiple set screws 264 of the type shown in FIG. 2B). Using multiple screws 264 can provide additional stability for the lead, particularly for long leads, and/or can provide multiple points by which to access and secure the lead. This arrangement can have particular benefits if the lead anchor 350 is positioned in the patient in such a way that a single aperture would be obscured or otherwise inaccessible.

FIG. 4 illustrates a lead anchor 450 having features generally similar to those described above with reference to FIGS. 2A-3. The lead anchor 450 further includes a plurality of apertures, identified individually as apertures 466a-466c, that are circumferentially offset from one another (e.g., in a spiral or helical arrangement). In addition to the benefits described above, the offset apertures 466a-466c can provide a practitioner with additional flexibility in securing the lead. For example, if the physician's access to one of the apertures 466a-466c is obstructed by the patient's tissue, the practitioner has multiple other apertures which may be more accessible for advancing a set screw and securing the lead. In further embodiments, the lead anchor 450 can include more or fewer apertures 466a-466c and the apertures can be aligned more or less along a longitudinal line or in another pattern or arrangement.

Certain embodiments of the technology described above can additionally or alternately include other features or methods that further improve lead securement. For example, in some embodiments, the restriction member can be formed from a shape-memory material so as to transform between a first configuration (in which a lead is freely positionable relative to an anchor sleeve) and a second configuration (in which the lead is removably and releasably secured). A representative shape memory material is nickel titanium. The restriction member can be activated (e.g., deformed) by applying heat, electricity, mechanical force, or other energy forms to transform between the first and second configuration. In certain embodiments, the shape-memory transition can occur after the energy is imparted via a tool. In other embodiments, the transition can occur when the anchor is transitioned from ambient conditions to the conditions in the human body (e.g., when body heat is applied to the shape-memory material). The use of shape-memory materials can be in addition to, or in lieu of, other locking mechanisms described herein (e.g., the set screw 264 illustrated in FIG. 2B).

In further embodiments, the lead securement device can have a clamshell configuration. For example, the lead securement device can include an upper and lower component or a single component that opens and closes like a book or clamshell. The lead securement device can accommodate one or more leads in an interior lumen while in an open configuration and can apply a compressive force to the lead(s) upon closing. The upper and lower components can be securably closed via snaps or other fastening mechanisms. Representative embodiments are described in further detail below with reference to FIGS. 9A-10D. In certain embodiments, the lumen can include barriers, such as posts or pivot points, that force the lead to take a non-linear path within the anchor sleeve. The tortuous path that results can inhibit or eliminate lead migration relative to the anchor. Similarly, in certain embodiments, a pre-shaped, curved lead body can be straightened for implanting with a stylet or introducer. When the stylet or introducer is removed, the lead can return to its original curved shape, which provides for improved anchor fixation.

In certain embodiments, chemical solutions can be applied to a lead to provide or improve lead fixation. For example, in one embodiment, a lead anchor can include a foam or other expansive material. The expansive material, when mixed with saline or other liquid, can expand and exert a compressive force on the lead, thereby holding the lead in place. In further embodiments, adhesives, such as UV quickset adhesives, can be applied to fix the lead in place. The adhesives can be dissolved, etched or otherwise chemically altered to release the lead. In a particular embodiment, the anchor can include multiple chambers. A first chamber can contain one component of a two-part adhesive (e.g., an epoxy) positioned along a lead/anchor interface. A second chamber separated by a membrane from the first chamber can include a second component of the two-part adhesive. In certain embodiments, the chambers are coaxial. When the membrane between the chambers is broken, the adhesives can intermix, triggering the curing process of the adhesive and thereby affixing the lead in place.

Figure 5A:
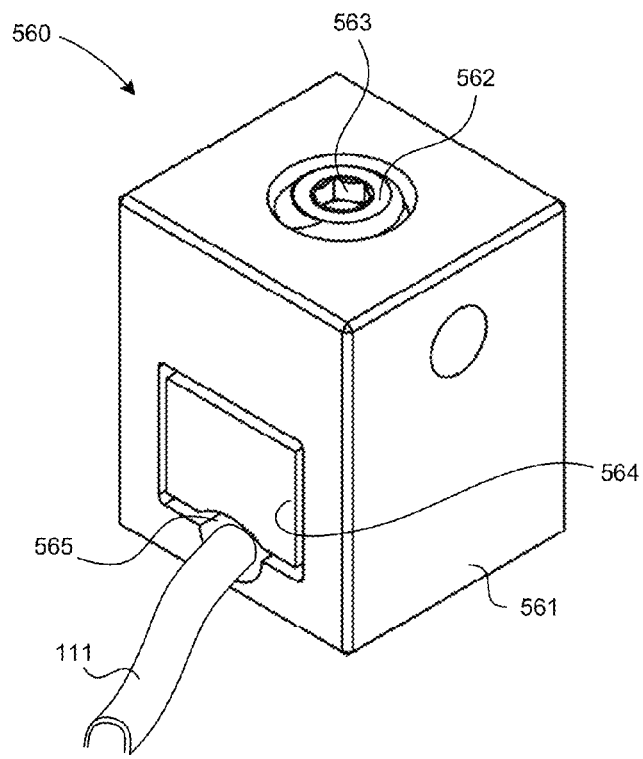
FIG. 5A is partially schematic, isometric illustration of a lead securement device having a press member in accordance with an embodiment of the present technology.
Figure 5B:
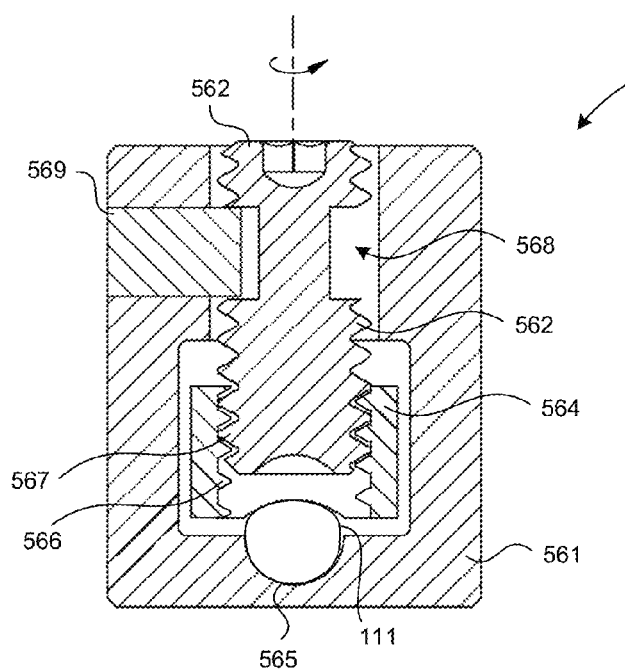
FIG. 5B is a partially schematic, cross-sectional illustration having an embodiment of the lead securement device shown in FIG. 5A.

FIGS. 5A and 5B illustrate a lead securement device 560 having a press member 564 configured in accordance with another aspect of the presently disclosed technology. For purposes of illustration, the securement device 560 in FIGS. 5A and 5B is shown without an anchor sleeve. In at least some embodiments, the securement device 560 and/or other anchor devices described below can be installed in an anchor sleeve, e.g., generally similar to the anchor sleeve 253 shown in FIG. 2A. In particular embodiments, the securement device 560 may be used to secure a lead or other signal delivery element in a pulse generator, a lead extension component, or a component that may releasably couple a lead or other signal delivery element to an external stimulator. Beginning with FIG. 5A, the lead securement device 560 includes a body 561, having a lead opening 565 positioned to receive a lead 111. The press member 564 is positioned within the body so as to move toward the lead 111 (e.g., to clamp the lead 111 in a secured position) and away from the lead 111 (e.g., to release the lead 111). The lead securement device 560 accordingly includes an actuator 562 (e.g., a set screw or plunger) that drives the press member 564 toward and away from the lead 111. The actuator 562 can include a hex key aperture 563 or other feature that allows the practitioner to rotate the actuator 562 with a hex key or other tool. The lead securement device 560 can be positioned within an anchor sleeve in a manner generally similar to that described in further detail below with reference to FIG. 6D.

FIG. 5B is a partially schematic, cross-sectional illustration of an embodiment of the lead securement device 560 shown in FIG. 5A. As shown in FIG. 5B, the press member 564 has an open interior with engagement features such as internal threads 566, and the actuator 562 has corresponding engagement features such as external threads 567 that mate with the internal threads 566. The actuator 562 can include a circumferentially-extending recess 568 that receives a retention element 569 (e.g., a pin) carried by the body 561. Accordingly, the actuator 562 remains captured within the body 561 so as to rotate with little or no axial motion. As it rotates, the actuator 562 drives the press body 564 toward and away from the lead opening 565, depending upon which direction the actuator 562 is rotated. The engagement features 566 and 567 may be optionally fully or partially coated with a material and/or otherwise treated to preferentially increase or control the friction therebetween for more accurate control of lead securement in operation. In some embodiments, such a coating and/or treatment may also be used on the surfaces of the press member 564 and/or body 561 that come in contact with the lead 111 so to limit or eliminate the lead's contact with metal. As shown in FIG. 5B, the actuator 562 has been activated to drive the press body 564 down to compress the lead 111 against the interior surface(s) of the lead cavity 565. The actuator 562 can be driven in the opposite direction to release the lead 111.

Figure 6A:
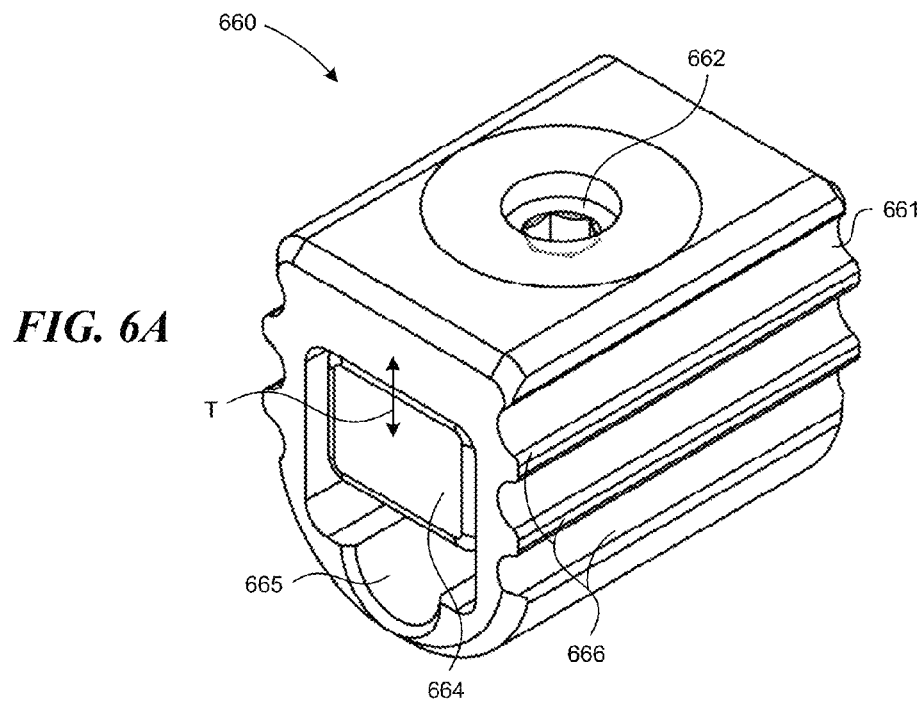
FIG. 6A is a partially schematic, isometric illustration of a lead securement device having a press member in accordance with another embodiment of the present technology.
Figure 6B:
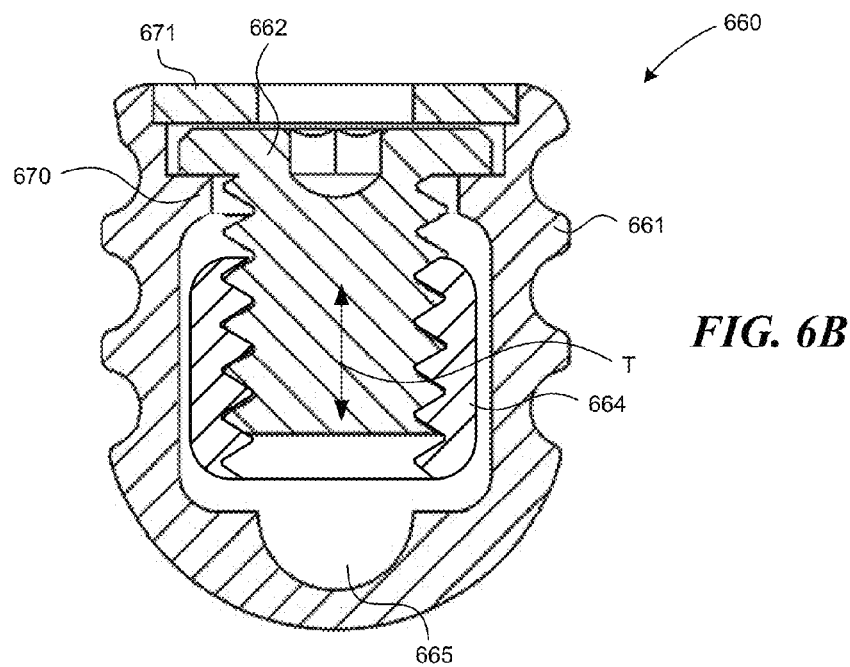
FIG. 6B is a partially schematic, cross-sectional illustration of an embodiment of the lead securement device shown in FIG. 6A.

FIGS. 6A and 6B illustrate a lead securement device 660 that includes a press member 664 having features distinct from those described above with reference to FIGS. 5A and 5B. Such a device 660 may in particular embodiments be used to secure a lead or other signal delivery element in a pulse generator, a lead extension component, or a component that may releasably couple a lead or other signal delivery element to an external stimulator. Referring first to FIG. 6A, the lead securement device 660 includes a body 661, a lead opening 665, a press member 664 positioned proximate to the lead opening 665, and an actuator 662 positioned to drive the press member 664 toward and away from the lead opening 665, as indicated by arrow T. In addition, the lead securement device 660 can include external features 666 positioned at the body 661. The external features 666 can include ridges, grooves, troughs, and/or other roughness elements that aid in securing the lead securement device 660 to a corresponding sleeve, as will be described further below with reference to FIG. 6D. The surfaces of the press member 664 and/or the lead opening 665 may be partially or completely coated with a plastic or polymer, and/or may otherwise be treated to increase friction with the lead and/or limit contact between the lead and metal components of the securement device 660.

Referring next to FIG. 6B, the actuator 662 is captured axially between a lip 670 extending inwardly from the body 661, and a washer or cap 671 (e.g., a retention element) positioned over the actuator 662. Accordingly, as the actuator 662 is rotated, it drives the press member 664 toward and away from the lead opening 665, as indicated by arrow T.

Figure 6C:
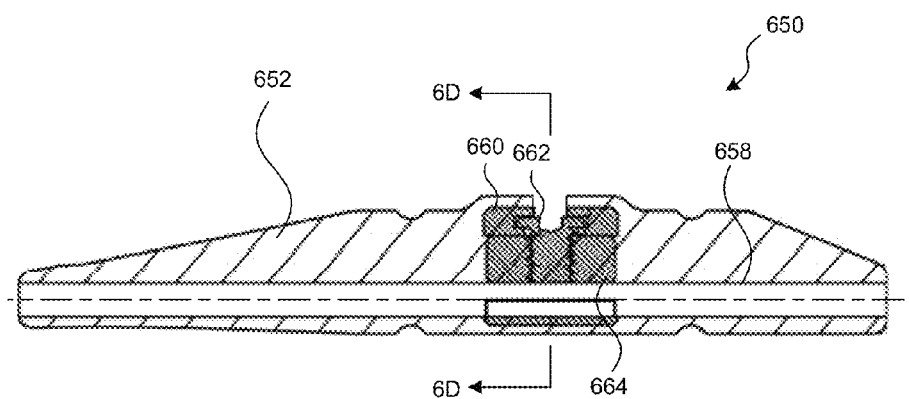
FIG. 6C is a partially schematic, cross-sectional illustration of a lead anchor that includes a lead securement device of the type shown in FIGS. 6A and 6B.
Figure 6D:
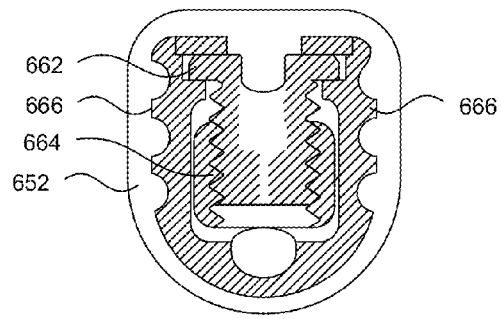
FIG. 6D is a partially schematic, isometric illustration of an embodiment of a lead anchor shown in FIG. 6C.

FIG. 6C is a partially schematic, cross-sectional illustration of an embodiment of the lead securement device 660 housed in a lead anchor 650 that includes an anchor sleeve 652. The lead anchor 650 also includes a lumen 658 positioned to receive a lead in a manner generally similar to that described above with reference to FIG. 2A. The external features 666 described above with reference to FIG. 6B extend inwardly and outwardly from the plane of FIG. 6C and accordingly are not visible in FIG. 6C. FIG. 6D, which illustrates a cross-section of the lead anchor 650, taken substantially along lines 6D-6D of FIG. 6C, illustrates the external features 666 engaged with the material forming the sleeve 652.

Figure 6E:
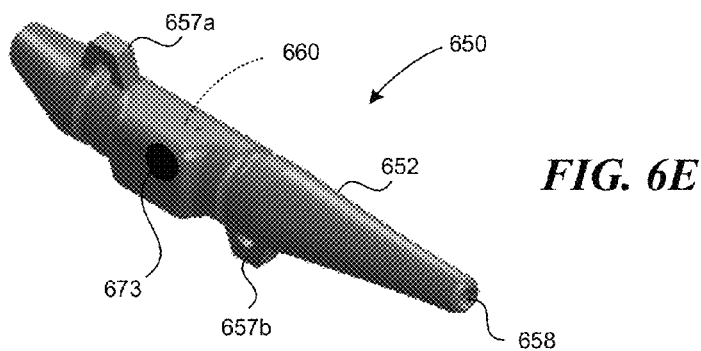
FIG. 6E is a partially schematic, isometric illustration of an embodiment of the lead anchor shown in FIGS. 6C and 6D.

FIG. 6E is a partially schematic, isometric illustration of the lead anchor 650. The lead securement device 660 (FIG. 6D) is not visible, but is contained within the sleeve 652. An aperture 673 extends through the sleeve 652 to allow access to the actuator 662 (FIG. 6C) of the lead securement device 660. The lead anchor 650 can further include tissue securing features 657a, 657b for securing the lead anchor 650 to the patient's tissue in a manner generally similar to that described above.

Figure 7A:
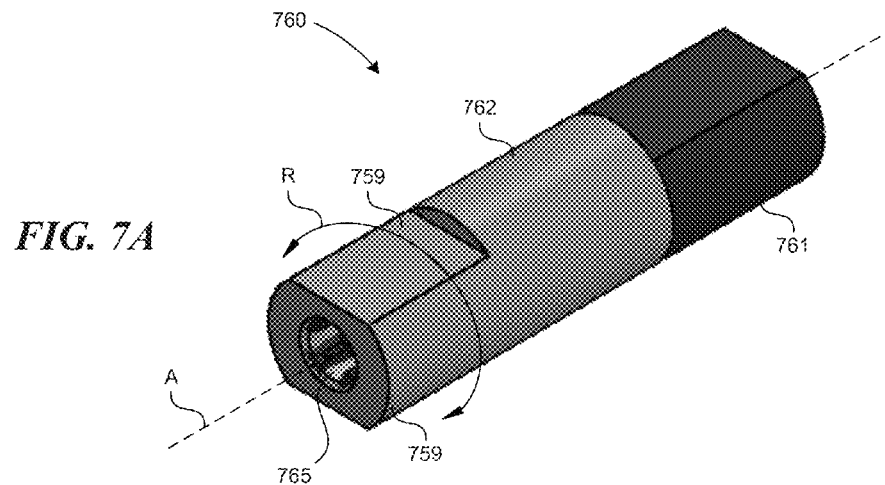
FIG. 7A is a partially schematic, isometric illustration of a lead securement device having a collet arrangement in accordance with another embodiment of the present technology.

FIG. 7A is a partially schematic, isometric illustration of a lead securement device 760 having a collet arrangement in accordance with another embodiment of the present technology. The lead securement device 760 can include a body 761 that extends at least partially into an actuator 762. The actuator 762 and the body 761 have lead openings 765, e.g., coaxial openings (one of which is visible in FIG. 7A), to receive a lead. The actuator 762 is rotatable about a rotation axis A as indicated by arrow R, e.g. by grasping flats 759 with the practitioner's fingers or a tool, to tighten the body 761 against a lead placed within the lead opening 765, as is described further below with reference to FIGS. 7B-7C.

Figure 7B:
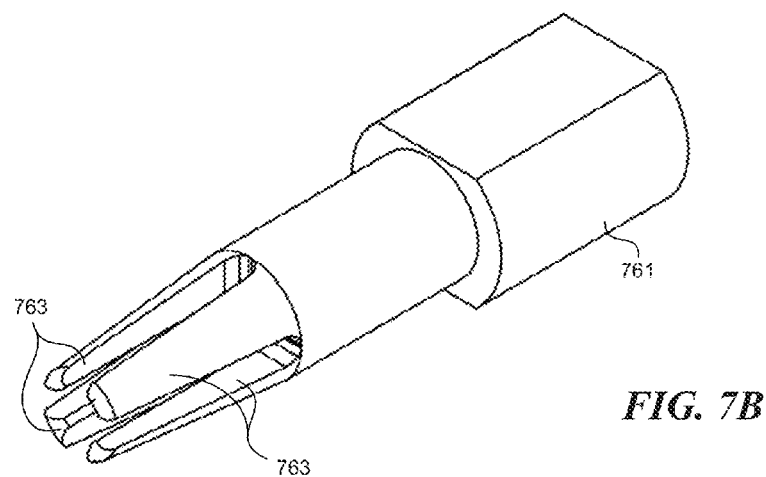
FIG. 7B is a partially schematic, isometric illustration of a portion of the lead securement device shown in FIG. 7A, having collet fingers in accordance with an embodiment of the present technology.

FIG. 7B is a partially schematic, isometric illustration of the body 761 shown in FIG. 7A, with the actuator 762 removed. The body 761 includes multiple collet fingers 763 (four are shown in FIG. 7B) that can be formed from metal, its alloys, plastic or another flexible, resilient material suitable for clamping against a lead.

Figure 7C:
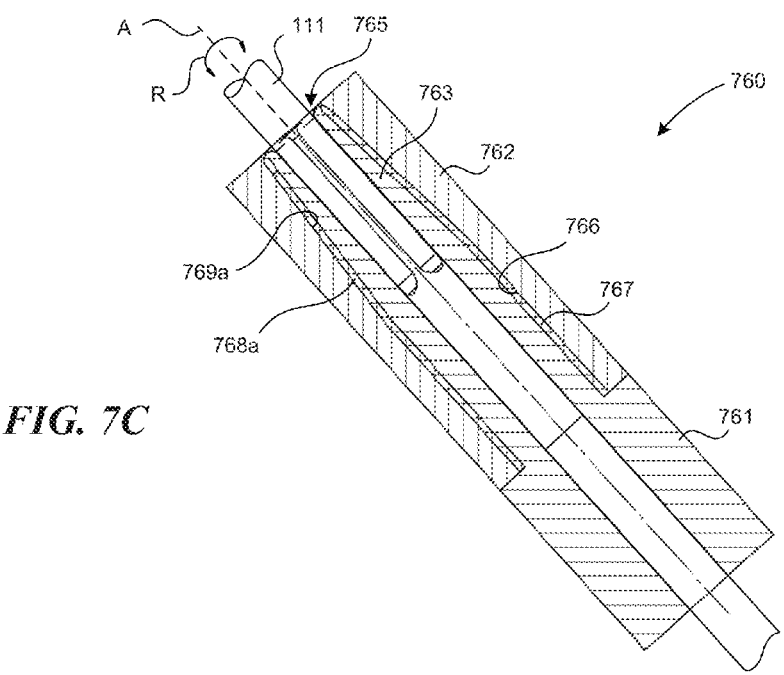
FIG. 7C is a partially schematic, cross-sectional illustration of the lead securement device shown in FIG. 7A.

FIG. 7C is a partially schematic, cross-sectional illustration of the lead securement device 760 shown in FIG. 7A. The body 761 includes engagement features such as external or male threads 767 (shown schematically) that mesh with corresponding engagement features such as internal or female threads 766 (shown schematically) carried by the actuator 762. The collet fingers 763 bear against an internal surface of the actuator 762. In a particular embodiment, an external angle 768*a* of the collet fingers 763 is approximately the same as an internal angle 769*a* of the actuator 762. In other embodiments (e.g., as described below with reference to FIG. 7D) these angles can be different. In any of these embodiments, as the actuator 762 is threaded along the body 761, the internal surface of the actuator 762 clamps the collet fingers 763 against a lead 111 positioned in the lead opening 765.

Figure 7D:
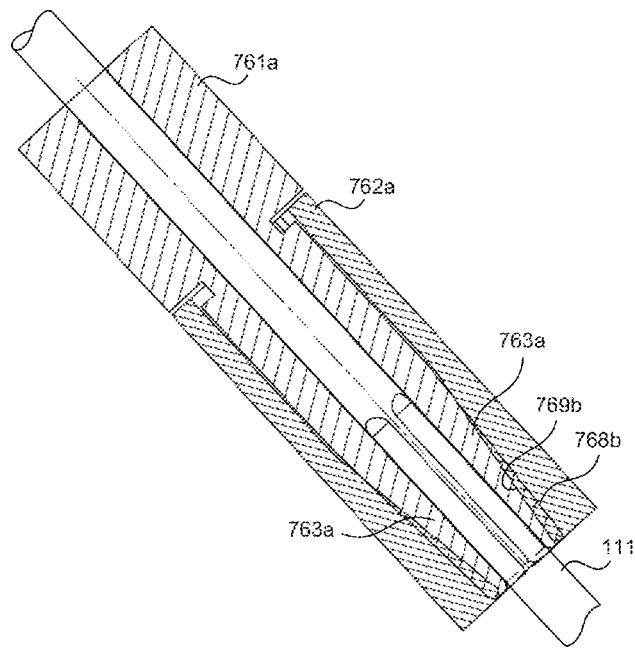
FIG. 7D is a partially schematic, cross-sectional illustration of a lead securement device having tapered surfaces in accordance with another embodiment of the present technology.

FIG. 7D is a partially schematic, cross-sectional illustration of a body 761*a* and an actuator 762*a* having different mating angles. For example, the body 761*a* can carry collet fingers 763*a* having an external angle 768*b* that is different than (e.g., greater than) an internal angle 769*b* of the actuator 762*a*. Accordingly, the actuator 762*a* can more positively engage the collet fingers 763*a* and clamp the fingers 763*a* against the lead 111.

Figure 8A:
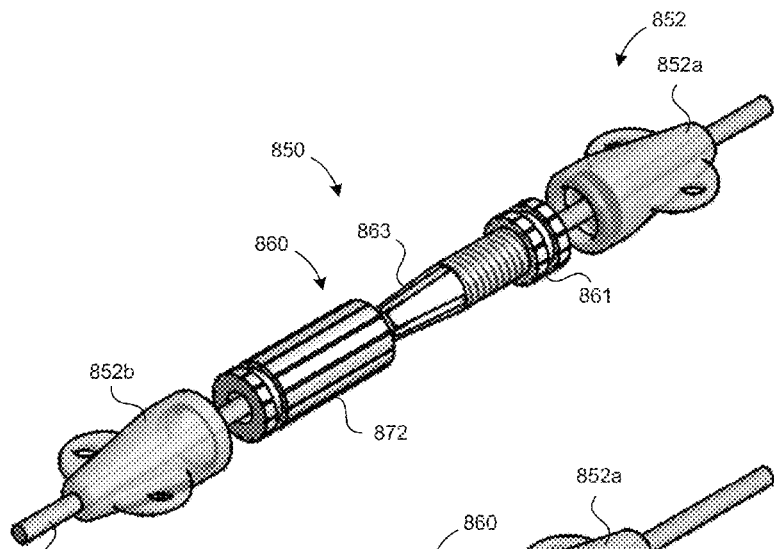
FIGS. 8A-8C are partially schematic, isometric illustrations of a device having rotary and lock features in accordance with an embodiment of the present technology.

FIG. 8A is a partially schematic, isometric illustration of an anchor 850 that includes a lead securement device 860 having a collet arrangement in accordance with another embodiment of the present technology. In one aspect of this embodiment, the lead securement device 860 includes a body 861 having spaced apart, flexible, resilient collet fingers 863, and an actuator 872 that fits over the collet fingers 863 and is threadably attached to the body 861. The lead securement device 860 can be partially housed in an anchor sleeve 852 that includes two separable anchor sleeve components 852*a*, 852*b*.

Figure 8B:
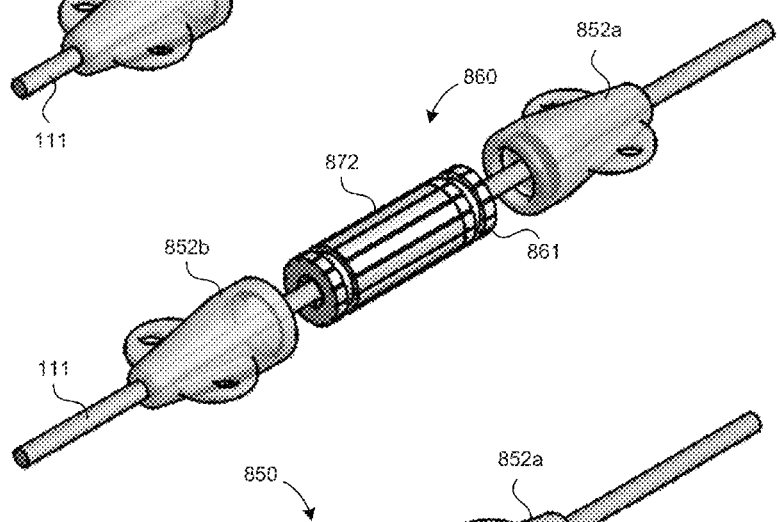
Figure 8C:
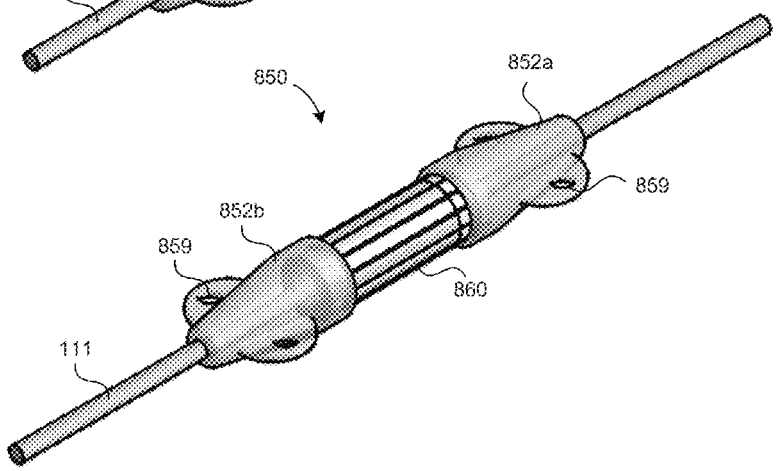

In operation, the components of the anchor 850 (e.g., the anchor sleeves 852*a*, 852*b*, the body 861 and the actuator 872) are threaded over the lead 111 in the order shown in FIG. 8A. As shown in FIG. 8B, the actuator 872 is then threaded onto the body 861 to tighten the collet fingers 863 (FIG. 8A) radially inwardly onto the lead 111. At this point, the lead securement device 860 is secured to the lead 111. In FIG. 8C, the anchor sleeve portions 852*a*, 852*b* are slid over the ends of the lead securement device 860. The anchor sleeve portions 852*a*, 852*b* include eyelets 859 that the practitioner then sutures to the patient to secure the anchor 850 in position. If the lead 111 is to be repositioned, the foregoing steps can be reversed to loosen the lead anchor 850. Then the lead 111 is moved relative to the anchor 850, and the forgoing steps are repeated to re-secure the lead anchor 850 to the lead 111.

Figure 9A:
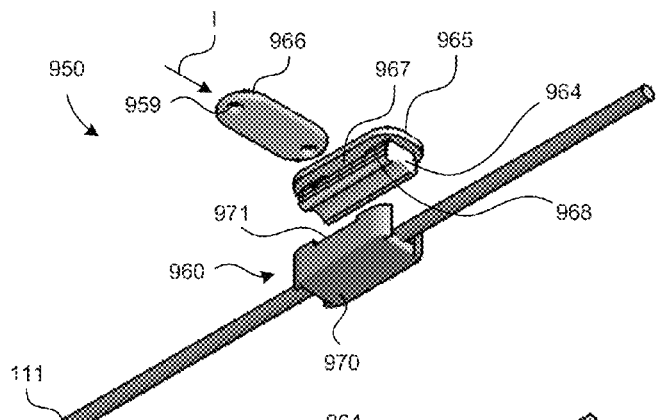
FIGS. 9A-9C are partially schematic, isometric illustrations of a securement device having linear engagement and lock features in accordance with another embodiment of the present technology.

FIG. 9A is a partially schematic, isometric illustration of a lead anchor 950 having a "push and lock" configuration in accordance with yet another embodiment of the present technology. In one aspect of this embodiment, the lead anchor 950 includes a securement device 960 that in turn includes a press member 964 received in a receptacle 970. The press member 964 can include a cap 965 and locking ribs 968 that engage with corresponding features in the receptacle 970. The lead anchor 950 can further include a suture member 966 having eyelets 959, that is removably received in a suture member slot 967 of the press member 964. The press member 964 is in turn received in the receptacle 970, with the suture member 966 received in a suture member recess 971 of the receptacle 970.

Figure 9B:
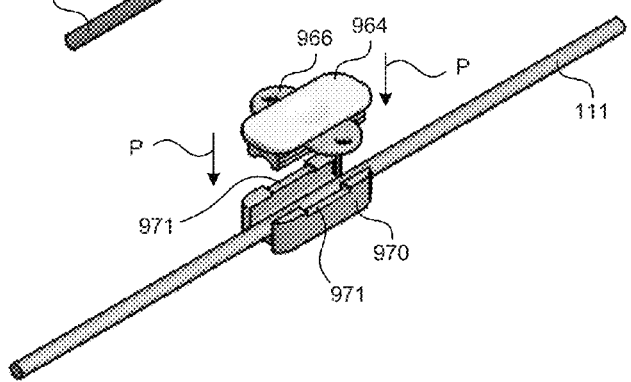

To begin the securing process, the lead 111 is positioned in the receptacle 970. The suture member 966 is then inserted into the suture member slot 967, as indicated by arrow I. Referring now to FIG. 9B, the press member 964 (with the suture member 966 is now positioned in the suture member slot 967, shown in FIG. 9A) is positioned over the receptacle 970. The press member 964 is then lowered and pressed into the receptacle 970, as indicated by arrows P, with the suture member 966 received in the suture member receptacles 971.

Figure 9C:
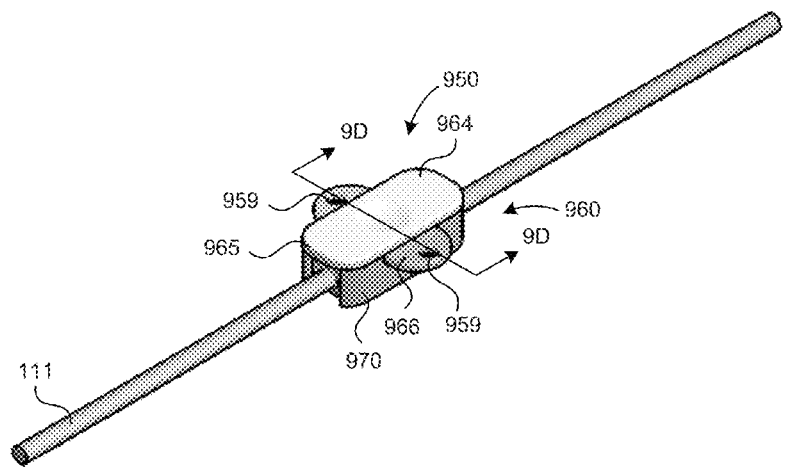

In FIG. 9C, the press member 964 has been fully inserted into the receptacle 970. Accordingly, the press member 964 presses the lead 111 against an upwardly facing surface of the receptacle 970 (not visible in FIG. 9C). In addition, the cap 965 is releasably locked in the receptacle 970, and presses the suture member 966 into the suture member recesses 971 (FIG. 9B). Accordingly, both the suture member 966 and the lead 111 are secured relative to the receptacle 970.

Figure 9D:
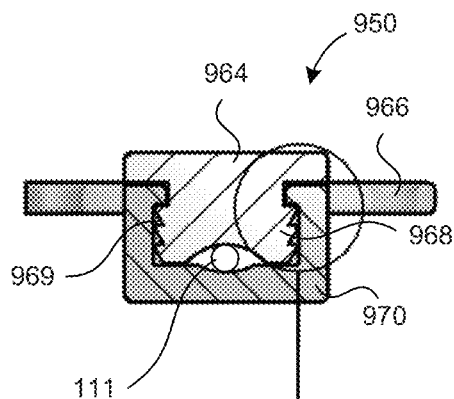
FIG. 9D and 9E are partially schematic, cross-sectional illustrations of a portion of the device shown in FIGS. 9A-9C.
Figure 9E:
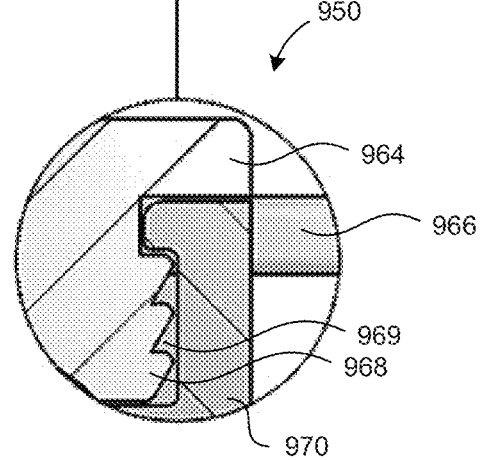

FIG. 9D is a partially schematic, cross-sectional illustration of the lead anchor 950, taken substantially along line 9D-9D of FIG. 9C. FIG. 9E is an enlarged view of a portion of the lead anchor 950 shown in FIG. 9D. Referring to FIGS. 9D and 9E together, the locking ribs 968 carried by the press member 964 are received in the receptacle 970 and interlock with corresponding features 969. The interlocking action of these features prevents or at least restricts the press member 964 from moving out of the receptacle 970, unless it is actively pried out by a practitioner, e.g., for repositioning the lead anchor 950 relative to the lead 111.

FIGS. 10A-10D illustrate a lead anchor 1050 having a "clamshell" arrangement in accordance with another embodiment of the present technology. FIG. 10A is a partially exploded view of a securement device 1060 of the lead anchor 1050, having a first portion 1061*a* rotatably coupled to a second portion 1061*b* with a hinge pin 1062. The first and second portions 1061*a*, 1061*b* can include an interlock 1063 that in turn includes a first element 1063*a* (e.g., a rib) carried by the first portion 1061*a*, and a second element 1063*b* (e.g., a lip) carried by the second portion 1061*b*.

FIG. 10B is a reverse view of the securement device 1060 shown in FIG. 10A, positioned around a lead 111. In addition, first and second portions 1052*a*, 1052*b* of a sleeve 1052 have been threaded onto the lead 111 on opposite sides of the lead securement device 1060. The interlock 1063 described above with reference to FIG. 10A can further include a finger tab 1063*c* that allows a practitioner to open the securement device 1060, should it become desirable to reposition the securement device 1060 relative to the lead 111.

Referring next to FIG. 10C, the first and second portions 1061*a*, 1061*b* have been releasably clamped around the lead 111 to secure the lead securement device 1060 in position. Then, as shown in a reverse view in FIG. 10D, the first and second portions 1052*a*, 1052*b* of the sleeve 1052 are slid over the ends of the lead securement device 1060 to releasably attach the sleeve 1052 to the lead securement device 1060. The practitioner can then suture the anchor 1050 using suture holes 1059 carried by the sleeve 1052.

FIGS. 11A-11E illustrate still another lead anchor 1150 having a guided piston arrangement for securing the lead anchor to the lead 111. Beginning with FIG. 11A, the lead anchor 1150 includes a securement device 1160 that in turn includes a body 1161 in which a piston 1162 is received. The piston carries a guide pin 1163 that is received in a spiral slot 1164. In preparation for securing the lead anchor 1150 to the lead 111, a sleeve 1152 (including a first portion 1152*a* and a second portion 1152*b*) are threaded along the lead 111 along with the lead securement device 1160, in the order shown in FIG. 11A.

Figure 11A:
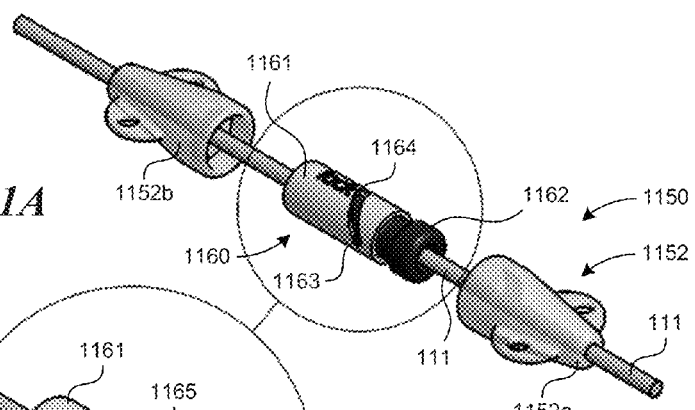
FIGS. 11A-11E are partially schematic, isometric illustrations of a lead securement device having a twist and lock configuration in accordance with another embodiment of the present technology.
Figure 11B:

FIG. 11B is an enlarged illustration of the lead securement device 1160, illustrating the piston 1162 in an unlocked position. In this position, the guide pin 1163 is located at one end of the guide slot 1164. The opposing end of the guide slot 1164 includes a detent 1165 that receives the guide pin 1163 and restricts it from further movement relative to the body 1161, unless directly acted upon by a user (e.g., a practitioner). To place the lead securement device 1160 in the locked position, the practitioner rotates the piston 1162 clockwise, as indicated by arrow R.

Figure 11C:
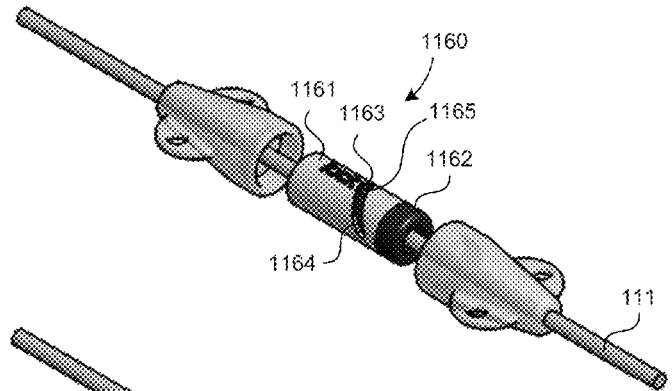
Figure 11D:
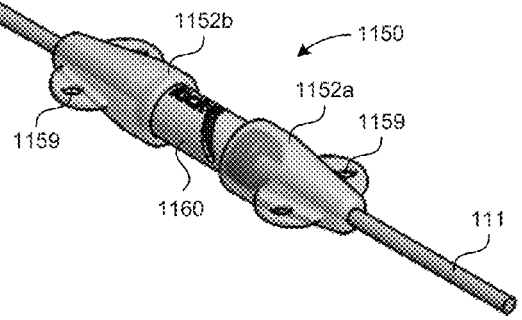

Referring next to FIG. 11C, the lead securement device 1160 has been placed in the locked position, with the piston 1162 advanced inwardly into the body 1161, and with the guide pin 1163 received in the detent 1165 at the end of the guide slot 1164. In FIG. 11D, the first and second portions 1152a, 1152b have been slid over the ends of the lead securement device 1160 to complete the process of securing the securement device 1160 to the lead 111. The practitioner can then suture the sleeve 1152 to the patient via suture openings 1159.

Figure 11E:
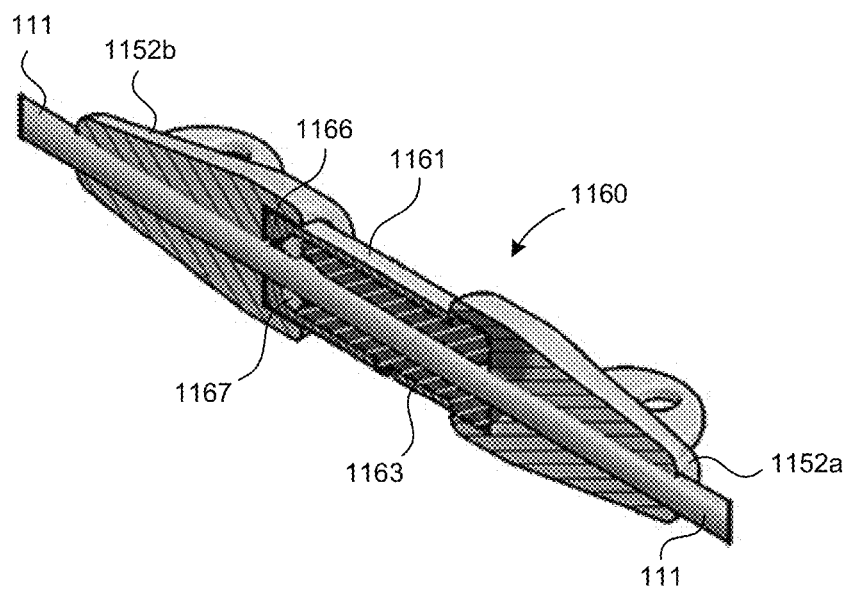

FIG. 11E is a partially schematic, cross-sectional illustration of the lead anchor and lead 111 in the secured position described above with reference to FIG. 11D. As shown in FIG. 11E, the piston 1163 bears against a resilient material 1167, for example, an O-ring. The body 1161 includes a tapered (e.g., conical) bearing surface 1166 against which the resilient material 1167 is located. As the piston 1163 is moved from the unlocked position (FIG. 11B) to the locked position (FIG. 11C), the piston 1163 drives toward the bearing surface 1166, forcing the resilient material 1167 radially inwardly and to the left as shown in FIG. 11E. Accordingly the resilient material 1167 bears radially inwardly against the lead 111, thus securing it in position relative to the lead securement device 1160. If it becomes desirable to release the lead securement device 1160 from the lead 111, the steps described above with reference to FIGS. 11A-11D are reversed, the lead 111 is then repositioned relative to the lead securement device 1160, and the foregoing steps are then repeated.

The embodiments described above offer several advantages over traditional systems and can inhibit lead migration to improve treatment outcomes. Traditionally, lead migration has been the single most common technical complication associated with spinal cord stimulation, with reported rates as high as 13.2%. (Cameron, T., *Safety and Efficacy of Spinal Cord Stimulation for the Treatment of Chronic Pain: A 20 Year Literature Review, J. Neurosurgery:* 100:254-267 (March 2004).) The systems disclosed herein provide securable yet reversible arrangements for attaching the lead to the lead anchor, and the lead anchor to the patient. The practitioner can easily verify when the lead is secured by the lead anchor. For example, in embodiments for which a torque wrench is used to advance a set screw, a practitioner can be assured of proper clamping by an auditory or palpable indication (e.g., a "click") that the set screw has been advanced a given gradation. This can remove much of variability and guesswork involved with anchoring leads.

An additional advantage is the ability to reposition a lead relative to the lead anchor. By repositioning rather than re-implanting the lead, the practitioner can reduce procedure time and improve placement accuracy as compared to traditional systems. Procedure time can be further reduced in embodiments for which an anchor secures more than a single lead. By having multiple leads within an anchor, the practitioner can additionally mitigate relative motion between the implanted leads. For example, embodiments of the "clamshell" arrangement and/or the "push and lock" arrangement described above with reference to FIGS. 10A-10D can accommodate two (or more) leads side by side, e.g., each in an individual, longitudinal extending groove.

From the foregoing, it will be appreciated that specific embodiments of the technology have been described herein for purposes of illustration, but that various modifications may be made without deviating from the technology. For example, in some embodiments the restriction member can have a fully circular cross-sectional shape but can readily compress and re-expand in a radial direction. In other embodiments, the anchor sleeve can include apertures arranged in patterns other than those specifically described above. Certain aspects of the technology described in the context of particular embodiments may be combined or eliminated in other embodiments. For example, in some embodiments the anchor may not have a set screw and the lead can be secured to the anchor by other mechanisms. Further, while advantages associated with certain embodiments have been described in the context of those embodiments, other embodiments may also exhibit such advantages and not all embodiments need necessarily exhibit such advantages to fall within the scope of the present technology. Accordingly, the present disclosure and associated technology can encompass other embodiments not expressly described or shown herein.

We claim:

1. A lead anchor, comprising:
   an implantable anchor sleeve having a lumen extending therethrough, the lumen being positioned to removably receive an implantable lead;
   a securement device within the anchor sleeve, the securement device including a lead opening aligned with and positioned along the lumen of the anchor sleeve to removably receive the implantable lead;
   a press member positioned within the securement device, the press member being slideable within the securement device toward the lead opening to clamp the implantable lead, and away from the lead opening to release the implantable lead;
   a rotatable actuator threadably engaged with the press member to move the press member toward the lead opening when rotated in a first direction, and move the press member away from the lead opening when rotated in a second direction opposite the first direction, the rotatable actuator including a recess; and
   a retention element fixedly carried by the securement device and projecting inwardly from the securement device and into the recess to at least restrict axial motion of the actuator toward and away from the lead opening.

2. The lead anchor of claim 1 wherein the retention element includes a pin projecting inwardly from the securement device into the recess to at least restrict axial motion of the actuator toward and away from the lead opening.

3. The lead anchor of claim 1 wherein the body of the securement device includes external grooves positioned to restrict relative motion between the securement device and the anchor sleeve.

4. The lead anchor of claim 1 wherein, the anchor sleeve has one or more suture eyelets positioned to receive suture thread to secure the anchor sleeve to patient tissue.

5. The lead anchor of claim 1 wherein the press member has a generally rectangular cross-sectional shape.

6. The lead anchor of claim 1 wherein the anchor sleeve is flexible.

7. The lead anchor of claim 1, further comprising the implantable lead.

* * * * *